United States Patent
Auerbach et al.

(10) Patent No.: US 10,294,494 B2
(45) Date of Patent: *May 21, 2019

(54) METHODS AND COMPOSITIONS FOR MODIFYING A TARGETED LOCUS

(71) Applicant: Regeneron Pharmaceuticals, Inc., Tarrytown, NY (US)

(72) Inventors: Wojtek Auerbach, Ridgewood, NJ (US); David Frendewey, New York, NY (US); Gustavo Droguett, New City, NY (US); Anthony Gagliardi, Hopewell Junction, NY (US); Junko Kuno, Holmes, NY (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/482,255

(22) Filed: Apr. 7, 2017

(65) Prior Publication Data

US 2017/0211099 A1 Jul. 27, 2017

Related U.S. Application Data

(63) Continuation of application No. 14/731,914, filed on Jun. 5, 2015, now Pat. No. 10,106,820.

(60) Provisional application No. 62/008,832, filed on Jun. 6, 2014, provisional application No. 62/017,916, filed on Jun. 27, 2014.

(51) Int. Cl.
| | | |
|---|---|---|
| *C12Q 1/04* | (2006.01) | |
| *C12N 15/90* | (2006.01) | |
| *C12N 15/64* | (2006.01) | |
| *A01K 67/027* | (2006.01) | |
| *C07K 14/725* | (2006.01) | |

(52) U.S. Cl.
CPC ........ *C12N 15/907* (2013.01); *A01K 67/0278* (2013.01); *C07K 14/7051* (2013.01); *C12N 15/64* (2013.01); *A01K 2217/072* (2013.01); *A01K 2227/105* (2013.01); *A01K 2267/0387* (2013.01); *C12N 2810/00* (2013.01)

(58) Field of Classification Search
None
See application file for complete search history.

(56) References Cited

U.S. PATENT DOCUMENTS

| | | | |
|---|---|---|---|
| 5,612,205 | A | 3/1997 | Kay et al. |
| 6,372,956 | B1 | 4/2002 | Goldsmith et al. |
| 6,566,579 | B1 | 5/2003 | Jaisser et al. |
| 7,294,754 | B2 | 11/2007 | Poueymirou et al. |
| 7,771,967 | B2 | 8/2010 | Huang et al. |
| 8,502,018 | B2 | 8/2013 | Murphy et al. |
| 8,697,359 | B1 | 4/2014 | Zhang |
| 9,228,208 | B2 | 1/2016 | Frendewey et al. |
| 9,546,384 | B2 | 1/2017 | Frendewey et al. |
| 2003/0134318 | A1 | 7/2003 | Case et al. |
| 2003/0175968 | A1 | 9/2003 | Golic et al. |
| 2004/0018626 | A1 | 1/2004 | Murphy et al. |
| 2004/0197317 | A1 | 10/2004 | Rao et al. |
| 2005/0144655 | A1 | 6/2005 | Economides et al. |
| 2007/0004041 | A1 | 1/2007 | Church et al. |
| 2008/0066197 | A1 | 3/2008 | Ying et al. |
| 2008/0113437 | A1 | 5/2008 | Joly et al. |
| 2008/0299580 | A1 | 12/2008 | DeKelver et al. |
| 2009/0055943 | A1 | 2/2009 | Economides et al. |
| 2010/0218264 | A1 | 8/2010 | Cui et al. |
| 2011/0119779 | A1 | 5/2011 | Shizuya et al. |
| 2011/0207321 | A1 | 8/2011 | Cost et al. |
| 2011/0307968 | A1 | 12/2011 | Auerbach et al. |
| 2012/0202251 | A1 | 8/2012 | Cornish et al. |
| 2012/0272349 | A1 | 10/2012 | Ochiya et al. |
| 2012/0315670 | A1 | 12/2012 | Jacobson et al. |
| 2013/0309670 | A1 | 11/2013 | Frendewey et al. |
| 2014/0068797 | A1 | 3/2014 | Doudna et al. |

(Continued)

FOREIGN PATENT DOCUMENTS

| | | |
|---|---|---|
| EP | 1360287 B1 | 9/2012 |
| WO | WO 2002/066630 A1 | 8/2002 |

(Continued)

OTHER PUBLICATIONS

Zhang et al., "The CRISPR/Cas9 system produces specific and homozygous targetd gene editing in rice in one generation," Plant Biotechnol. J., vol. 12(6), pp. 797-807, May 23, 2014.
"Stem Cells: Scientific Progress and Future Research Directions," National Institute of Health, Department of Health and Human Services, (2001).
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Benders et al., "Cloning whole bacterial genomes in yeast," Nucleic Acids Res., vol. 38(8), pp. 2558-2569, Mar. 7, 2010.

(Continued)

*Primary Examiner* — Channing S Mahatan
(74) *Attorney, Agent, or Firm* — Yongjin Choi; Alston & Bird LLP

(57) ABSTRACT

Methods and compositions are provided for modifying one or more target loci in a cell. Such methods comprise providing a cell comprising a first polynucleotide encoding a first selection marker operably linked to a first promoter active in the cell, wherein the first polynucleotide further comprises a first recognition site for a first nuclease agent. A first nuclease agent is introduced into a cell, wherein the first nuclease agent induces a nick or double-strand break at the first recognition site. Further introduced into the cell is a first targeting vector comprising a first insert polynucleotide flanked by a first and a second homology arm that correspond to a first and a second target site located in sufficient proximity to the first recognition site. At least one cell is then identified comprising in its genome the first insert polynucleotide integrated at the target locus.

43 Claims, 3 Drawing Sheets

Specification includes a Sequence Listing.

(56) References Cited

U.S. PATENT DOCUMENTS

| | | | |
|---|---|---|---|
| 2014/0273226 | A1 | 9/2014 | Wu |
| 2014/0273234 | A1 | 9/2014 | Zhang et al. |
| 2014/0301990 | A1 | 10/2014 | Gregory et al. |
| 2014/0309487 | A1 | 10/2014 | Lee et al. |
| 2014/0310828 | A1 | 10/2014 | Lee et al. |
| 2014/0342456 | A1 | 11/2014 | Mali et al. |
| 2014/0349400 | A1 | 11/2014 | Jakimo et al. |
| 2015/0079680 | A1 | 3/2015 | Bradley et al. |
| 2015/0140664 | A1 | 5/2015 | Byrne et al. |
| 2015/0159174 | A1 | 6/2015 | Frendewey et al. |
| 2015/0159175 | A1 | 6/2015 | Frendewey et al. |
| 2015/0376650 | A1 | 12/2015 | Auerbach et al. |
| 2015/0376651 | A1 | 12/2015 | Frendewey et al. |
| 2016/0024529 | A1 | 1/2016 | Carstens |
| 2016/0046960 | A1 | 2/2016 | Frendewey et al. |
| 2016/0060657 | A1 | 3/2016 | Frendewey et al. |
| 2016/0090607 | A1 | 3/2016 | Conway et al. |
| 2016/0108369 | A1 | 4/2016 | Kuno et al. |
| 2016/0122774 | A1 | 5/2016 | Duchateau et al. |
| 2016/0145646 | A1 | 5/2016 | Frendewey et al. |
| 2016/0177339 | A1 | 6/2016 | Voronina et al. |
| 2016/0257967 | A1 | 9/2016 | Russell et al. |
| 2017/0067078 | A1 | 3/2017 | Frendewey et al. |
| 2017/0204430 | A1 | 7/2017 | Lee et al. |
| 2017/0275611 | A1 | 9/2017 | Bradley et al. |

FOREIGN PATENT DOCUMENTS

| | | | |
|---|---|---|---|
| WO | WO 2003/087341 | A2 | 10/2003 |
| WO | WO 2006/044962 | A1 | 4/2006 |
| WO | WO 2007/117410 | A2 | 10/2007 |
| WO | WO 2008/151081 | A1 | 12/2008 |
| WO | WO 2011/051390 | A1 | 5/2011 |
| WO | WO 2011/078665 | A1 | 6/2011 |
| WO | WO 2011/154927 | A2 | 12/2011 |
| WO | WO 2011/158009 | A1 | 12/2011 |
| WO | WO 2012/012667 | A2 | 1/2012 |
| WO | WO 2012/018726 | A1 | 9/2012 |
| WO | WO 2012/129198 | A1 | 9/2012 |
| WO | WO 2013/063361 | A1 | 5/2013 |
| WO | WO 2013/163394 | A1 | 10/2013 |
| WO | WO 2013/169802 | A1 | 11/2013 |
| WO | WO 2013/176772 | A1 | 11/2013 |
| WO | WO 2014/104878 | A1 | 7/2014 |
| WO | WO 2014/143381 | A1 | 9/2014 |
| WO | WO 2014/172489 | A2 | 10/2014 |
| WO | WO 2014/186585 | A2 | 11/2014 |
| WO | WO 2014/191518 | A1 | 12/2014 |
| WO | WO 2014/205192 | A2 | 12/2014 |
| WO | WO 2015/040402 | A1 | 3/2015 |
| WO | WO 2015/052231 | A2 | 4/2015 |
| WO | WO 2015/077290 | A2 | 5/2015 |
| WO | WO 2015/086798 | A2 | 6/2015 |
| WO | WO 2015/088643 | A1 | 6/2015 |
| WO | WO 2015/116969 | A2 | 8/2015 |
| WO | WO 2015/163733 | A1 | 10/2015 |
| WO | WO 2015/166272 | A2 | 11/2015 |
| WO | WO 2015/188109 | A1 | 12/2015 |
| WO | WO 2015/200805 | A2 | 12/2015 |
| WO | WO 2016/061374 | A1 | 4/2016 |
| WO | WO 2016/081923 | A2 | 5/2016 |
| WO | WO 2016/100819 | A1 | 6/2016 |
| WO | WO 2016/142719 | A1 | 9/2016 |

OTHER PUBLICATIONS

Berdien, et al., "TALEN-mediated editing of endogenous T-cell receptors facilitates efficient reprogramming of T lymphocytes by lentiviral gene transfer," Gene Therapy, 21, 539-548 (2014).
Bernardini et al., "Site-specific genetic engineering of the Anopheles gambiae Y chromosome," Proc. Natl. Acad. Sci. USA, vol. 111(21), pp. 7600-7605, May 12, 2014.
Byrne et al., "Multi-kilobase homozygous targeted gene replacement in human induced pluripotent stem cells," Nucleic Acids Research, Vo. 43(3), p. e21, 2014 (epub Nov. 20, 2014).
Choulika et al., "Induction of Homologous Recombination in Mammalian Chromosomes by Using the I-SceI System of *Saccharomyces cerevisiae*," Mol. Cell. Biol., vol. 15(4), pp. 1968-1973, 1995.
Cobb and Zhao, "Direct cloning of large genomic sequences," Nature Biotechnology, 2012, vol. 30(5), pp. 405-406.
Cong et al., "Multiplex Genome Engineering Using CRISPR/Cas Systems," Science, vol. 339(6121), pp. 819-823 plus Supplemental Materials, Jan. 3, 2013.
Cong, et al., "Multiplex genome engineering using CRISPR/Cas systems," Science, 2013, vol. 339(6121), pp. 819-823.
Cui, et al., "Targeted integration in rat and mouse embryos with zinc-finger nucleases," Nature Biotechnology, vol. 29, No. 1, 64-68 (Dec. 12, 2010).
Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.
Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.
Doudna et al., "The new frontier of genome engineering with CRISPR-Cas9," Science, vol. 346(6213), pp. 1258096-1-1258096-9, Nov. 28, 2014.
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Flisikowska, et al., "Efficient Immunoglobulin Gene Disruption and Targeted Replacement in Rabbit Using Zinc Finger Nucleases," Plos one, vol. 6 Issue 6 (Jun. 2011).
Frendewey ,"VelociGene: Large-scale Modification of Rodent Genomes," Wellcome Trust Advanced Course: Genetic Engineering of Mammalian Stem Cells, Mar. 13, 2014.
Frendewey, "VelociGene: Large-scale Modification of Rodent Genomes," Wellcome Trust Advanced Course: Genetic Engineering of Mammalian Stem Cells, Feb. 20, 2015.
Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.
Gennequin, et al., "CRISPR/Cas-induced double-strand breaks boost the frequency of gene replacements for humanizing the mouse Cnr2 gene," Biochem. Biophys. Res. Commun., (2013), http://dx.doi.org/10.1016/j.bbrc.2013.10.138.
Gratz et al., "Genome Engineering of *Drosophila* with the CRISPR RNA-Guided Cas9 Nuclease," Genetics, vol. 194, pp. 1029-1035, 2013. (published May 2013).
Gratz et al., "Highly Specific and Efficient CRISPR/Cas9-Catalyzed Homology-Directed Repair in *Drosophila*," Genetics, vol. 196(4), pp. 961-971 plus Supporting Information, Jan. 29, 2014.
Jallepalli et al., "Securin is required for chromosomal stability in human cells," Cell, vol. 105(4), pp. 445-447, May 18, 2001.
Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.
Jasin, et al., "Repair of Strand Breaks by Homologous Recombination," Cold Spring Harb. Perspect. Biol., vol. 5(11), p. a012740, Nov. 1, 2013.
Johnson, et al., "A rapid assay to quantify the cleavage efficiency of custom-designed nucleases in planta," Plant Mol Biol, 82:207-221 (2013).
Kashimada et al., "Sry: the master switch in mammalian sex determination," Development, vol. 137(23), pp. 3921-3930, Dec. 2, 2010.
Kato et al., "Production of Sry knockout mouse using TALEN via oocyte injection," Scientific Reports, vol. 3, p. 3136, 2013 (published Nov. 5, 2013).

(56) References Cited

OTHER PUBLICATIONS

Konermann et al., "Genome-scale transcriptional activation by an engineered CRISPR-Cas9 complex," Nature, vol. 517(7536), pp. 583-588, published online Dec. 10, 2014.
Kuijpers et al., "One-step assembly and targeted integration of multigene constructs assisted by the I-SceI meganuclease in *Saccharomyces cerevisiae*," FEMS Yeast Res., vol. 13(8), pp. 769-781, Oct. 7, 2013.
Kuno et al., "Generation of fertile and fecund F0 XY female mice from XY ES cells," Transgenic Research, vol. 24(1), pp. 19-29, 2014 (epub Aug. 3, 2014).
Kuroiwa, et al., "Sequential targeting of the genes encoding immunoglobulin-µ and prion protein in cattle," Nature Genetics, vol. 36, No. 7, (Jul. 2004).
Li et al., "Germline Competent Embryonic Stem Cells Derived from Rat Blastocysts," Cell, vol. 135, pp. 1299-1310, 2008.
Li et al., "Optimization of Genome Engineering Approaches with the CRISPR/Cas9 System," PLoS One, vol. 9(8), p. e105779, Aug. 28, 2014.
Liu et al., "A one-step cloning method for the construction of somatic cell gene targeting vectors: application to production of human knockout cell lines," BMC Biotechnol., vol. 12, p. 71, Oct. 9, 2012.
Lombaro, et al., "Gene editing in human stem cells using zinc finger nucleases and integrase-defective lentiviral vector delivery," Nature Biotechnology, 2007, vol. 25(11), pp. 1298-1306.
Macdonald, et al., "Precise and in situ genetic humanization of 6 Mb of mouse immunoglobulin genes," PNAS, vol. 111, No. 14: 5147-5152, (Apr. 8, 2014).
Mali et al., "RNA-Guided Human Genome Engineering via Cas9," Science, vol. 339(6121), pp. 823-826 plus Supplemental Materials, Jan. 3, 2013.
Mali, et al., "CAS9 transcriptional activators for target specificity screening and paired nickases for cooperative genome engineering," Nature Biotechnology, vol. 31(9), pp. 833-838 plus Supplementary Information, Aug. 1, 2013.
Mali, et al., "Cas9 as a versatile tool for engineering biology," Nature Methods, vol. 10(10), pp. 957-963, 2013.
Mashiko et al., "Generation of mutant mice by pronuclear injection of circular plasmid expressing Cas9 and single guided RNA," Sci. Rep., vol. 3, p. 3355, Nov. 27, 2013.
Mashimo et al., "Generation of knockout rats with X-linked severe combined immunodeficiency (X-SCID) using zinc finger nucleases," PLoS One, vol. 5(1), p. e8870, 2010.
Musser, "Rodent," Brittanica. Retrieved from the Internet May 31, 2016: http://www.britannica.com/animal/rodent/.
Narsinh, et al., "Gene Correction in Human Embryonic and Induced Pluripotent Stem Cells: Promise and Challenges Ahead", Molecular Therapy, vol. 18, No. 6, pp. 1061-1063, (Jun. 2010).
Ni et al., "Inactivation of an integrated antibiotic resistance gene in mammalian cells to re-enable antibiotic selection," BioTechniques, vol. 56, pp. 198-201, Apr. 2014.
PCT International Preliminary Report on Patentability for application PCT/US2013/038165 dated Oct. 28, 2014.
PCT International Preliminary Report on Patentability for application PCT/US2014/034412 dated Oct. 30, 2015.
PCT International Preliminary Report on Patentability for application PCT/US2015/034503 dated Dec. 6, 2016.
PCT International Search Report and Written Opinion of the International Searching Authority for application PCT/US2014/060788 dated Jan. 26, 2015.
PCT International Search Report and Written Opinion of the International Searching Authority for application PCT/US2015/038001 dated Feb. 25, 2016.
PCT International Search Report and Written Opinion of the International Searching Authority for application PCT/US2015/062023 dated May 13, 2016.
PCT International Search Report and Written Opinion of the International Searching Authority for application PCT/US2015/066681 dated Mar. 29, 2016.
PCT International Search Report for application PCT/US2015/034503 dated Sep. 8, 2015.
PCT Written Opinion of the International Searching Authority for application PCT/US2015/034503 dated Sep. 8, 2015.
PCT/US2013/038165 International Search Report and Written Opinion dated Jul. 12, 2013.
PCT/US2014/034412 International Search Report and Written Opinion of the Searching Authority dated Oct. 9, 2014.
PCT/US2015/038001 Invitation of Pay Additional Fees dated Nov. 13, 2015.
PCT/US2015/062023 Invitation of Pay Additional Fees dated Feb. 8, 2016.
Port et al., "Optimized CRISPR/Cas tools for efficient germline and somatic genome engineering in *Drosophila*," Proc. Natl. Acad. Sci. U.S.A., vol. 111(29), pp. E2967-E2976 plus Supporting Information, Jul. 7, 2014.
Porteus, et al., "Gene targeting using zinc finger nucleases," Nature Biotechnology, vol. 23(8), pp. 967-973, 2005.
Poueymirou et al., "F0 generation mice fully derived from gene-targeted embryonic stem cells allowing immediate analysis," Nature Biotechnology, Epub Dec. 24, 2006, vol. 25(1):91-99.
Quinn et al., "A Site-Specific, Single-Copy Transgenesis Strategy to Identify 5' Regulatory Sequences of the Mouse Testis-Determining Gene Sry," PLoS One, vol. 9(4), p. e94813, Apr. 2014.
Ran et al., "Double nicking by RNA-guided CRISPR Cas9 for enhanced genome editing specificity," Cell, vol. 154, pp. 1380-1389, 2013.
Ran et al., "Genome engineering using the CRISPR-Cas9 system," Nature Protocols, vol. 8(11), pp. 2281-2308, Oct. 24, 2013.
Ran et al., "In vivo genome editing using *Staphylococcus aureus* Cas9," Nature, vol. 520(7546), pp. 186-191, Apr. 1, 2015.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Shan et al., "Targeted genome modification of crop plants using a CRISPR-Cas system," Nature Biotechnology, vol. 31(8), pp. 686-688, Aug. 1, 2013.
Stemgent Product Specification Sheet, PD0325901, pp. 1-2 (2012).
Tong et al., "Generating gene knockout rats by homologous recombination in embryonic stem cells," Nature Protocols, vol. 6(6), pp. 827-844, 2011 (epub May 26, 2011).
U.S. Appl. No. 13/870,280 Final Rejection dated Oct. 15, 2015.
U.S. Appl. No. 13/870,280, Requirement for Restriction/Election dated Jul. 22, 2014.00000000.
U.S. Appl. No. 14/254,715 Final Office Action dated Nov. 30, 2015.
U.S. Appl. No. 14/254,715, Non-Final Office Action dated Apr. 21, 2016.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Advisory Action dated Aug. 15, 2016.
U.S. Appl. No. 14/314,866, Final Office Action dated Apr. 26, 2016.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/314,866, Final Office Action dated Jun. 4, 2015.
U.S. Appl. No. 14/515,503, Non-Final Office Action dated May 20, 2016.
U.S. Appl. No. 14/515,503, Requirement for Restriction/Election dated Mar. 4, 2016.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 14/731,914 , Requirement for Restriction/Election dated Dec. 31, 2015.
U.S. Appl. No. 14/731,914, Non-Final Office Action dated Jun. 17, 2016.
U.S. Appl. No. 14/731,914, Notice of Allowance dated Jan. 27, 2017.

(56) References Cited

OTHER PUBLICATIONS

U.S. Appl. No. 14/751,807, Requirement for Restriction/Election dated Aug. 26, 2016.
U.S. Appl. No. 14/926,773, Non-Final Office Action dated May 6, 2016.
U.S. Appl. No. 14/926,773, Requirement for Restriction/Election dated Feb. 16, 2016.
U.S. Appl. No. 14/928,180, Advisory Action dated Aug. 22, 2016.
U.S. Appl. No. 14/928,180, Final Office Action dated Jun. 6, 2016.
U.S. Appl. No. 13/870,280, Advisory Action dated Jan. 5, 2016.
U.S. Appl. No. 13/870,280, Non-Final Office Action dated Mar. 13, 2015.
U.S. Appl. No. 14/254,715, Requirement for Restriction/Election dated Jun. 4, 2015.
U.S. Appl. No. 14/928,180, Non-Final Office Action dated Jan. 5, 2016.
Wang et al., "One-Step Generation of Mice Carrying Mutations in Multiple Genes by CRISPR/Cas-Mediated Genome Engineering," Cell, vol. 153, pp. 910-918 plus supplemental materials, 2013. (published May 2013).
Wang et al., "Talen-mediated editing of the mouse Y chromosome," Nature Biotechnology, vol. 31(6), p. 530-532, 2013 (epub May 12, 2013).
Wen et al., "Completely ES Cell-Derived Mice Produced by Tetraploid Complementation Using Inner Cell Mass (ICM) Deficient Blastocysts," PLoS One, vol. 9(4), e94730, Apr. 14, 2014.
Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.
Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.
Yu et al., "Highly Efficient Genome Modifications Mediated by CRISPR/Cas9 in *Drosophila*," Genetics, vol. 195, pp. 289-291 plus supporting information, Sep. 2013.
Zhang et al., "Biallelic targeting of expressed genes in mouse embryonic stem cells using the Cas9 system," Methods, vol. 69(2), pp. 171-178, Jun. 12, 2014.
Turan et al., "Recombinase-mediated cassette exchange (RMCE)—a rapidly-expanding toolbox for targeted genomic modifications," Gene, 515(1):1-27, (2013).
U.S. Appl. No. 14/731,914, Non-Final Office Action dated Aug. 24, 2017.
U.S. Appl. No. 14/731,914, Notice of Allowance dated Jun. 8, 2018.
Kosicki et al., "Repair of double-strand breaks induced by CRISPR-Cas9 leads to large deletions and complex rearrangements," Nat. Biotechnol., 36(8): 765-771, (Jul. 16, 2018).
Bloor, et al., "An Efficient Method of Selectable Marker Gene Excision by Xer Recombination for Gene Replacement in Bacterial Chromosomes," Appl. Environ. Microbiol., 72(4):2520-2525, (2006).
Melton, et al., "Stability of HPRT marker gene expression at different gene-targeted loci: observing and overcoming a position effect," Nucleic Acids Res., 25(19):3937-3943, (1997).

SEQUENCE LISTING

```
<160> NUMBER OF SEQ ID NOS: 21

<210> SEQ ID NO 1
<211> LENGTH: 23
<212> TYPE: DNA
<213> ORGANISM: Artificial Sequence
<220> FEATURE:
<223> OTHER INFORMATION: a target locus that is linked to a guide RNA
      (gRNA)
<220> FEATURE:
<221> NAME/KEY: misc_feature
<222> LOCATION: (2)...(21)
<223> OTHER INFORMATION: n = A, T, C, or G

<400> SEQUENCE: 1
gnnnnnnnnn nnnnnnnnnn ngg                                           23

<210> SEQ ID NO 2
<211> LENGTH: 80
<212> TYPE: RNA
<213> ORGANISM: Artificial Sequence
<220> FEATURE:
<223> OTHER INFORMATION: a guide RNA (gRNA)

<400> SEQUENCE: 2
guuuuagagc uagaaauagc aaguuaaaau aaggcuaguc cguuaucaac uugaaaaagu    60
ggcaccgagu cggugcuuuu                                               80

<210> SEQ ID NO 3
<211> LENGTH: 42
<212> TYPE: RNA
<213> ORGANISM: Artificial Sequence
<220> FEATURE:
<223> OTHER INFORMATION: a guide RNA (gRNA)

<400> SEQUENCE: 3
guuuuagagc uagaaauagc aaguuaaaau aaggcuaguc cg                      42

<210> SEQ ID NO 4
<211> LENGTH: 30
<212> TYPE: RNA
<213> ORGANISM: Artificial Sequence
<220> FEATURE:
<223> OTHER INFORMATION: a crRNA

<400> SEQUENCE: 4
guuuuagagc uagaaauagc aaguuaaaau                                    30

<210> SEQ ID NO 5
<211> LENGTH: 33
<212> TYPE: RNA
<213> ORGANISM: Artificial Sequence
<220> FEATURE:
<223> OTHER INFORMATION: a crRNA

<400> SEQUENCE: 5
guuuuagagc uagaaauagc aaguuaaaau aag                                33

<210> SEQ ID NO 6
<211> LENGTH: 26
<212> TYPE: RNA
<213> ORGANISM: Artificial Sequence
<220> FEATURE:
<223> OTHER INFORMATION: a crRNA

<400> SEQUENCE: 6
```
gaguccgagc agaagaagaa guuuua                                       26

<210> SEQ ID NO 7
<211> LENGTH: 12
<212> TYPE: RNA
<213> ORGANISM: Artificial Sequence
<220> FEATURE:
<223> OTHER INFORMATION: a tracrRNA

<400> SEQUENCE: 7
aaggcuaguc cg                                                      12

<210> SEQ ID NO 8
<211> LENGTH: 50
<212> TYPE: RNA
<213> ORGANISM: Artificial Sequence
<220> FEATURE:
<223> OTHER INFORMATION: a tracrRNA

<400> SEQUENCE: 8
aaggcuaguc cguuaucaac uugaaaaagu ggcaccgagu cggugcuuuu             50

<210> SEQ ID NO 9
<211> LENGTH: 40
<212> TYPE: DNA
<213> ORGANISM: Artificial Sequence
<220> FEATURE:
<223> OTHER INFORMATION: Neo-ZFN(1,2): NUCLEASE BINDING SITE/cut site

<400> SEQUENCE: 9
gggcgcccgg ttcttttgt caagaccgac ctgtccggtg                         40

<210> SEQ ID NO 10
<211> LENGTH: 36
<212> TYPE: DNA
<213> ORGANISM: Artificial Sequence
<220> FEATURE:
<223> OTHER INFORMATION: ZFN(3,4): NUCLEASE BINDING SITE/cut site

<400> SEQUENCE: 10
ccggttcttt tgtcaagac cgacctgtcc ggtgcc                             36

<210> SEQ ID NO 11
<211> LENGTH: 42
<212> TYPE: DNA
<213> ORGANISM: Artificial Sequence
<220> FEATURE:
<223> OTHER INFORMATION: ZFN(1,2): NUCLEASE BINDING SITE/cut site

<400> SEQUENCE: 11
tgcgatcgct gcggccgatc ttagccagac gagcgggttc gg                     42

<210> SEQ ID NO 12
<211> LENGTH: 36
<212> TYPE: DNA
<213> ORGANISM: Artificial Sequence
<220> FEATURE:
<223> OTHER INFORMATION: Hyg-ZFN(3,4): NUCLEASE BINDING SITE/cut site

<400> SEQUENCE: 12
cgctgcggcc gatcttagcc agacgagcgg gttcgg                            36

<210> SEQ ID NO 13
<211> LENGTH: 20
<212> TYPE: RNA
<213> ORGANISM: Artificial Sequence
<220> FEATURE:
<223> OTHER INFORMATION: gRNA Neo Crispr#1

<400> SEQUENCE: 13
ugcgcaagga acgcccgucg                                              20

<210> SEQ ID NO 14
<211> LENGTH: 20
<212> TYPE: RNA
<213> ORGANISM: Artificial Sequence
<220> FEATURE:
<223> OTHER INFORMATION: gRNA Neo Crispr#2

<400> SEQUENCE: 14
ggcagcgcgg cuaucguggc                                              20

<210> SEQ ID NO 15
<211> LENGTH: 20
<212> TYPE: RNA
<213> ORGANISM: Artificial Sequence
<220> FEATURE:
<223> OTHER INFORMATION: gRNA Neo Crispr#3

<400> SEQUENCE: 15
acgaggcagc gcggcuaucg                                              20

<210> SEQ ID NO 16
<211> LENGTH: 20
<212> TYPE: RNA
<213> ORGANISM: Artificial Sequence
<220> FEATURE:
<223> OTHER INFORMATION: gRNA Neo Crispr#4

<400> SEQUENCE: 16
gcucugaugc cgccguguuc                                              20

<210> SEQ ID NO 17
<211> LENGTH: 20
<212> TYPE: RNA
<213> ORGANISM: Artificial Sequence
<220> FEATURE:
<223> OTHER INFORMATION: gRNA Hyg Crispr#1

<400> SEQUENCE: 17
acgagcgggu ucggcccauu                                              20

<210> SEQ ID NO 18
<211> LENGTH: 20
<212> TYPE: RNA
<213> ORGANISM: Artificial Sequence
<220> FEATURE:
<223> OTHER INFORMATION: gRNA Hyg Crispr#2

<400> SEQUENCE: 18
cuuagccaga cgagcggguu                                              20

<210> SEQ ID NO 19
<211> LENGTH: 20
<212> TYPE: RNA
<213> ORGANISM: Artificial Sequence
<220> FEATURE:
<223> OTHER INFORMATION: gRNA Hyg Crispr#3

<400> SEQUENCE: 19
gccgaucuua gccagacgag                                              20

```
<210> SEQ ID NO 20
<211> LENGTH: 20
<212> TYPE: RNA
<213> ORGANISM: Artificial Sequence
<220> FEATURE:
<223> OTHER INFORMATION: gRNA Hyg Crispr#4

<400> SEQUENCE: 20
cgaccugaug cagcucucgg                                                    20

<210> SEQ ID NO 21
<211> LENGTH: 25
<212> TYPE: DNA
<213> ORGANISM: Artificial Sequence
<220> FEATURE:
<223> OTHER INFORMATION: a target locus that is linked to a guide RNA
      (gRNA)
<220> FEATURE:
<221> NAME/KEY: misc_feature
<222> LOCATION: (3)...(23)
<223> OTHER INFORMATION: n = A, T, C, or G

<400> SEQUENCE: 21
ggnnnnnnnn nnnnnnnnnn nnngg                                              25
```

METHODS AND COMPOSITIONS FOR MODIFYING A TARGETED LOCUS

CROSS-REFERENCE TO RELATED APPLICATIONS

This application is a continuation of U.S. patent application Ser. No. 14/731,914, filed Jun. 5, 2015, which claims the benefit of U.S. Provisional Application No. 62/008,832, filed Jun. 6, 2014, and of U.S. Provisional Application No. 62/017,916, filed Jun. 27, 2014, each of which is herein incorporated by reference in its entirety.

FIELD

The methods and compositions relate to the field of molecular biology. In particular, methods and compositions are provided for modifying a targeted locus in a cell.

REFERENCE TO A SEQUENCE LISTING SUBMITTED AS A TEXT FILE VIA EFS WEB

This application includes an electronic sequence listing in a file named 493877SEQLIST.TXT, created Apr. 7, 2017, and containing 4.46 kilobytes, which is hereby incorporated by reference in its entirety for all purposes.

BACKGROUND

Homologous recombination using targeting vectors that are specifically designed to add, delete, or replace a particular nucleic acid sequence at a genomic locus is a popular approach to achieving a desired genomic modification in a cell. A nuclease that is specifically engineered to introduce a nick or a double-strand break at or near a target locus can be used in combination with a targeting vector to enhance the efficiency of homologous recombination at the target locus.

Although the art of targeted modification through homologous recombination has advanced considerably over the last two decades, difficulties still remain with achieving an acceptable targeting efficiency using targeting vectors. Methods are needed which improve the efficacy and efficiency by which targeted modifications are produced.

SUMMARY

Methods and compositions are provided for modifying one or more target loci in a cell.

In some embodiments, methods for modifying a target locus in a cell are provided and comprise: (a) providing a cell comprising a target locus that comprises a first polynucleotide encoding a first selection marker operably linked to a first promoter active in the cell, wherein the first polynucleotide further comprises a first recognition site for a first nuclease agent, (b) introducing into the cell (i) a first nuclease agent, wherein the first nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site; and, (c) identifying at least one cell comprising the first insert polynucleotide integrated at the target locus.

In some embodiments, a method for modifying a target locus in a cell, comprises: (a) providing a cell comprising a first target locus comprising a first polynucleotide encoding a first selection marker operably linked to a first promoter, wherein the first polynucleotide further comprises a first recognition site for a first nuclease agent, (b) introducing into the cell: (i) one or more expression constructs encoding a first nuclease agent which is operably linked to a promoter active in the cell, wherein the first nuclease agent induces a nick or a double-strand break at a first recognition site in the first polynucleotide, thereby disrupting expression or activity of the first selection marker; and (ii) a first targeting vector comprising a first insert polynucleotide comprising a second polynucleotide that encodes a second selection marker operably linked to a second promoter, wherein the first insert nucleic acid is flanked by a first and a second homology arm corresponding to a first and a second target site located in the first target locus; and (c) identifying a modified cell comprising the first insert nucleic acid at the first target locus, wherein the modified cell has the activity of the second selection marker but does not have the activity of the first selection marker, and wherein the first and the second selection markers are different.

In one embodiment, the target locus is in the genome of the cell. In another embodiment, the target locus is located in a vector in the cell. In one embodiment, the nick or double strand break at the first recognition site disrupts the activity of the first selection marker. In yet a further embodiment, the identifying step (c) comprises culturing the cells under conditions that allow identification of cells that do not have an activity of the first selection marker. In one embodiment, the first polynucleotide comprising the first selection marker is flanked by a first target site and a second target site. In one embodiment, the identifying step (c) comprises identifying at least one cell comprising the first insert polynucleotide integrated at the first and the second target site. In one embodiment, the first insert polynucleotide comprises: (a) a first polynucleotide of interest; and, (b) a second polynucleotide encoding a second selection marker operably linked to a second promoter active in the cell, wherein the second polynucleotide comprises a second recognition site for a second nuclease agent.

In one embodiment, the method further comprises (a) introducing into the cell comprising the first insert polynucleotide integrated at the target locus, (i) a second nuclease agent, wherein the second nuclease agent induces a nick or double-strand break at the second recognition site; and, (ii) a second targeting vector comprising a second insert polynucleotide flanked by a third and a fourth homology arm corresponding to a third and a fourth target site located in sufficient proximity to the second recognition site; and, (b) identifying at least one cell comprising the second insert polynucleotide integrated at the target locus. In one embodiment, the nick or double-strand break at the second recognition site disrupts the activity of the second selection marker. In one embodiment, the identifying step (b) comprises culturing the cell under conditions that allow identification of cells that do not have the activity of the second selection marker. In one embodiment, the second polynucleotide comprising the second selectable marker is flanked by the third target site and the fourth target site. In one embodiment, the identifying step (b) comprises identifying at least one cell comprising the second insert polynucleotide integrated at the third and the fourth target site.

In one embodiment, the second insert polynucleotide comprises: (a) a second polynucleotide of interest; and, (b) a third polynucleotide encoding a third selection marker operably linked to a third promoter active in the cell, wherein the third polynucleotide comprises a third recognition site for a third nuclease agent. In one embodiment, the first nuclease agent is different from the second nuclease agent. In one embodiment, the first selection marker is different from the second selection marker. In one embodiment, the first and the third nuclease recognition site are identical to one another and are different from the second nuclease recognition site; and, the first and the third nuclease agent are identical to one another and are different from the second nuclease agent. In one embodiment, the first and the third selection markers are identical. In one embodiment, one of the first, the second or the third selection marker imparts resistance to an antibiotic. In one embodiment, the antibiotic comprises G418, hygromycin, blasticidin, neomycin, or puromycin. In one embodiment, one of the first, the second or the third selection marker is operably linked to an inducible promoter, and expression of the selectable marker is toxic to the cell. In one embodiment, the first, the second or the third selection marker comprises hypoxanthine-guanine phosphoribosyltransferase (HGPRT) or thymidine kinase of Herpes simplex virus (HSV-TK). In one embodiment, said cell is a prokaryotic cell. In one embodiment, the cell is a eukaryotic cell. In one embodiment, the eukaryotic cell is a mammalian cell. In one embodiment, the mammalian cell is a non-human mammalian cell. In one embodiment, the mammalian cell is from a rodent. In one embodiment, the rodent is a rat or a mouse.

In one embodiment, the cell is a pluripotent cell. In one embodiment, the mammalian cell is a human induced pluripotent stem (iPS) cell. In one embodiment, the pluripotent cell is a non-human embryonic stem (ES) cell. In one embodiment, the pluripotent cell is a mouse embryonic stem (ES) cell or a rat embryonic stem (ES) cell. In one embodiment, the pluripotent cell is a hematopoietic stem cell. In one embodiment, the pluripotent cell is a neuronal stem cell. In one embodiment, the mammalian cell is a human fibroblast.

In one embodiment, the combined use of the first targeting vector with the first nuclease agent results in an increased targeting efficiency compared to the use of the first targeting vector alone. In one embodiment, the targeting efficiency of the first targeting vector is increased at least 2-fold compared to the use of the first targeting vector alone.

In one embodiment, the first or the second nuclease agent comprises an expression construct comprising a nucleic acid sequence encoding the nuclease agent, and wherein the nucleic acid is operably linked to a fourth promoter active in the cell. In one embodiment, the first or the second nuclease agent is an mRNA encoding a nuclease. In one embodiment, the first or the second nuclease agent is a zinc finger nuclease (ZFN). In one embodiment, the first or the second nuclease agent is a Transcription Activator-Like Effector Nuclease (TALEN). In one embodiment, the first or the second nuclease agent is a meganuclease.

In one embodiment, the first or the second nuclease agent comprises a Clustered Regularly Interspaced Short Palindromic Repeats (CRISPR)-associated (Cas) protein and a guide RNA (gRNA). In one embodiment, the guide RNA (gRNA) comprises (a) a Clustered Regularly Interspaced Short Palindromic Repeats (CRISPR) RNA (crRNA) that targets the first, the second, or the third recognition sites; and (b) a trans-activating CRISPR RNA (tracrRNA). In one embodiment, the first or the second recognition sites are immediately flanked by a Protospacer Adjacent Motif (PAM) sequence. In one embodiment, the genomic locus of interest comprises the nucleotide sequence of SEQ ID NO: 1. In one embodiment, the Cas protein is Cas9. In one embodiment, the gRNA comprises: (a) the chimeric RNA of the nucleic acid sequence of SEQ ID NO: 2; or, (b) the chimeric RNA of the nucleic acid sequence of SEQ ID NO: 3. In one embodiment, the crRNA comprises SEQ ID NO: 4; SEQ ID NO: 5; or SEQ ID NO: 6. In one embodiment, the tracrRNA comprises SEQ ID NO: 7 or SEQ ID NO: 8.

In one embodiment, the first, the second, and/or the third recognition site is located in an intron, an exon, a promoter, a promoter regulatory region, or an enhancer region of the first, the second, or the third selection marker. In one embodiment, the first target site and the second target site are immediately adjacent to the first recognition site. In one embodiment, the first target site and the second target site are about 10 nucleotides to about 14 kb from first recognition site. In one embodiment, the third target site and the fourth target site are immediately adjacent to the second recognition site. In one embodiment, the third target site and the fourth target site are about 10 nucleotides to about 14 kb from the second recognition site.

In one embodiment, a sum total of the first homology arm and the second homology arm is at least about 10 kb. In one embodiment, a sum total of the third homology arm and the fourth homology arm is at least about 10 kb. In one embodiment, the first insert polynucleotide ranges from about 5 kb to about 300 kb in length. In one embodiment, the second insert polynucleotide ranges from about 5 kb to about 300 kb in length.

In one embodiment, integration of the first insert polynucleotide into the target locus results in a knockout, a knock-in, a point mutation, a domain swap, an exon swap, an intron swap, a regulatory sequence swap, a gene swap, or a combination thereof. In one embodiment, integration of the second insert polynucleotide into the target locus results in a knockout, a knock-in, a point mutation, a domain swap, an exon swap, an intron swap, a regulatory sequence swap, a gene swap, or a combination thereof.

In one embodiment, the first insert polynucleotide comprises a polynucleotide of interest comprising a human polynucleotide. In one embodiment, the second insert polynucleotide comprises a polynucleotide of interest comprising a human polynucleotide. In one embodiment, the first insert polynucleotide comprises a polynucleotide of interest comprising a region of the T cell receptor alpha locus.

In one embodiment, the second insert polynucleotide comprises a polynucleotide of interest comprising a region of the T cell receptor alpha locus. In one embodiment, the first or the second insert polynucleotide comprise a polynucleotide of interest comprising at least one variable region gene segment and/or a joining region gene segment of the T cell receptor alpha locus. In one embodiment, the region of the T cell receptor alpha locus is from a human.

In one embodiment, the first insert polynucleotide comprises a polynucleotide of interest comprising an unrearranged human immunoglobulin heavy chain variable region nucleic acid sequence operably linked to a non-human immunoglobulin heavy chain constant region nucleic acid sequence.

In one embodiment, the identifying step is carried out via a modification of allele (MOA) assay. In one embodiment, the first insert polynucleotide comprises a polynucleotide of interest comprising a nucleic acid sequence that is homologous or orthologous to the nucleic acid sequence in a genome of the cell. In one embodiment, the second insert polynucleotide comprises a nucleic acid sequence that is homologous or orthologous to the nucleic acid sequence in a genome of the cell. In one embodiment, the first insert polynucleotide comprises a polynucleotide of interest comprising an exogenous nucleic acid sequence. In one embodiment, the second insert polynucleotide comprises a polynucleotide of interest comprising an exogenous nucleic acid sequence.

In some embodiments, the methods for modifying a target locus in a cell comprise: (a) providing a cell comprising a first target locus comprising a nucleic acid encoding a first selection marker operably linked to a first promoter; (b) introducing into the cell (i) one or more expression constructs encoding a Cas protein and a first guide RNA (gRNA), each of which is operably linked to a promoter active in the cell, wherein the Cas protein induces a nick or a double-strand break at a first gRNA target site in the first nucleic acid, thereby disrupting expression or activity of the first selection marker, and (ii) a first targeting vector comprising a first insert nucleic acid comprising a second nucleic acid that encodes a second selection marker operably linked to a second promoter, wherein the first insert nucleic acid is flanked by a first and a second homology arm corresponding to a first and a second target site located in the first target locus; and (c) identifying a modified cell comprising the first insert nucleic acid at the first target locus, wherein the modified cell has the activity of the second selection marker but does not have the activity of the first selection marker, and wherein the first and the second selection markers are different. In one embodiment, the first gRNA does not hybridize to the first insert nucleic acid. In one embodiment, the target locus of interest is located in the genome of the cell. In another embodiment, the target locus of interest is located in a vector in the cell. In one embodiment, the identifying step (c) comprises culturing the cell under conditions that allow identification of the modified cell that has activity of the second selection marker but does not have the activity of the first selection marker.

In one embodiment, the method further comprises (d) introducing into the modified cell comprising the first insert nucleic acid at the first target locus (i) one or more nucleic acids encoding the Cas protein and a second gRNA, each of which is operably linked to the promoter active in the modified cell, wherein the Cas protein induces the nick or double-strand break at a second gRNA target site in the first insert nucleic acid comprising the second nucleic acid, thereby disrupting expression or activity of the second selection marker, and (ii) a second targeting vector comprising a second insert nucleic acid comprising a third nucleic acid encoding a third selection marker operably linked to a third promoter, wherein the second insert nucleic acid is flanked by third and fourth homology arms corresponding to a third and a fourth target site located in a second target locus; and (e) identifying a second modified cell comprising the second insert nucleic acid at the second target locus, wherein the second modified cell has the activity of the third selection marker but does not have the activity of the second selection marker, wherein the second and the third selection markers are different. In one embodiment, the first and the second target loci are located immediately adjacent to each other. In another embodiment, the first or the second target locus is located about 10 nucleotides to about 14 kb, about 10 nucleotides to about 100 nucleotides, about 100 nucleotides to about 500 nucleotides, about 500 nucleotides to about 1000 nucleotides, about 1 kb to about 5 kb, about 5 kb to about 10 kb, or about 10 kb to about 14 kb from the first or the second gRNA target site. In one embodiment, the second gRNA does not hybridize to the second insert nucleic acid. In one embodiment, the identifying step (e) comprises culturing the modified cell under conditions that allow identification of the second modified cell that has activity of the third selection marker but does not have the activity of the second selection marker.

In one embodiment, the method further comprises (f) introducing into the second modified cell comprising the second insert nucleic acid at the second target locus: (i) the one or more expression constructs encoding the Cas protein and a third gRNA, each of which operably linked to the promoter active in the second modified cell, wherein the Cas protein induces the nick or double-strand break at a third gRNA target site in the second insert nucleic acid comprising the third nucleic acid, thereby disrupting expression or activity of the third selection marker, and (ii) a third targeting vector comprising a third insert nucleic acid comprising a fourth nucleic acid that encodes a fourth selection marker operably linked to a fourth promoter, wherein the third insert nucleic acid is flanked by fifth and six homology arms corresponding to fifth and sixth target sites located in a third target locus; and (g) identifying a third modified cell comprising the third insert nucleic acid at the third target locus, wherein the third modified cell has the activity of the fourth selection marker but does not have the activity of the third selection marker, wherein the third and the fourth selection markers are different. In one embodiment, the second and third target loci are located immediately adjacent to each other. In another embodiment, the second or the third target locus is located about 10 nucleotides to about 14 kb from the first or the second gRNA target site.

In one embodiment, the first, the second, the third, or the fourth marker imparts resistance to an antibiotic. In one embodiment, the antibiotic comprises G418, hygromycin, blastocidin, neomycin, or puromycin. In one embodiment, the first, the second, the third, or the fourth selection markers comprise hypoxanthine-guanine phosphoribosyltransferase (HGPRT) or thymidine kinase of Herpes simplex virus (HSV-TK). In one embodiment, the first, the second, or the third gRNAs comprises (i) a nucleotide sequence that hybridizes to the first, the second or the third gRNA target site and (ii) a trans-activating CRISPR RNA (tracrRNA). In one embodiment, the first, the second, or the third target locus is located in close proximity to the first, the second or the third gRNA target site such that the nick or the double-strand break at the gRNA target site promotes homologous recombination of the targeting vector at the target locus. In one embodiment, the Cas protein is Cas9. In one embodiment, the first, the second, or the third gRNA target site is immediately flanked by a Protospacer Adjacent Motif (PAM) sequence.

In one embodiment, the cell is a prokaryotic cell. In another embodiment, the cell is a eukaryotic cell. In one embodiment, the eukaryotic cell is a mammalian cell. In one embodiment, the mammalian cell is a fibroblast cell. In one embodiment, the mammalian cell is a human fibroblast cell. In one embodiment, the mammalian cell is a non-human mammalian cell. In one embodiment, the mammalian cell is from a rodent. In one embodiment, the rodent is a rat, a mouse, or a hamster.

In one embodiment, the eukaryotic cell is a pluripotent cell. In one embodiment, the pluripotent cell is a hematopoietic stem cell or a neuronal stem cell. In one embodiment, the pluripotent cell is a human induced pluripotent stem (iPS) cell. In one embodiment, the pluripotent cell is a mouse embryonic stem (ES) cell or a rat embryonic stem (ES) cell.

In one embodiment, the first, the second, or the third gRNA target site is located in an intron, an exon, a promoter, or a promoter regulatory region in the first, the second, or the third nucleic acid that encodes the first, the second, or the third selection marker. In one embodiment, the first, second, or third targeting vector is at least about 10 kb. In one embodiment, the first, the second, or the third insert nucleic acid ranges from about 5 kb to about 300 kb.

In one embodiment, the first, second, or third insert nucleic acid comprises a genomic region of the human T cell receptor alpha locus. In one embodiment, the genomic region comprises at least one variable region gene segment and/or a joining region gene segment of the human T cell receptor alpha locus.

In one embodiment, the first and the third selection markers are the same. In one embodiment, the first and the third selection markers are the same and the second and the fourth selection markers are the same. In one embodiment, the first and the third gRNAs are the same.

Further provided are methods and compositions are provided for modifying a target locus in a cell. Such methods comprise providing a cell comprising a target locus comprising a first polynucleotide encoding a first selection marker operably linked to a first promoter active in the cell, wherein the first polynucleotide further comprises a first recognition site for a first nuclease agent. A first nuclease agent is introduced into the cell, wherein the first nuclease agent induces a nick or double-strand break at the first recognition site. Further introduced into the cell is a first targeting vector comprising a first insert polynucleotide flanked by a first and a second homology arm that correspond to a first and a second target site located in sufficient proximity to the first recognition site. At least one cell is then identified comprising the first insert polynucleotide integrated at the target locus.

Also provided are methods for modifying a target locus in a cell comprising: (a) providing a cell comprising a target locus that comprises a first polynucleotide encoding a first selection marker operably linked to a first promoter active in the cell, wherein the first polynucleotide further comprises a first recognition site for a first nuclease agent, (b) introducing into the cell (i) a first nuclease agent, wherein the first nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site; and, (c) identifying at least one cell comprising the first insert polynucleotide integrated at the target locus. In one embodiment, the target locus is in the genome of the cell. In another embodiment, the target locus is located in a vector in the cell. In one embodiment, the nick or double-strand break at the first recognition site disrupts the activity of the first selection marker. In yet a further embodiment, the identifying step (c) comprises culturing the cells under conditions that allow identification of cells that do not have an activity of the first selection marker. In one embodiment, the first polynucleotide comprising the first selection marker is flanked by a first target site and a second target site. In one embodiment, the identifying step (c) comprises identifying at least one cell comprising the first insert polynucleotide integrated at the first and the second target site. In one embodiment, the first insert polynucleotide comprises: (a) a first polynucleotide of interest; and, (b) a second polynucleotide encoding a second selection marker operably linked to a second promoter active in the cell, wherein the second polynucleotide comprises a second recognition site for a second nuclease agent.

In one embodiment, the method further comprises (a) introducing into the cell comprising the first insert polynucleotide integrated at the target locus, (i) a second nuclease agent, wherein the second nuclease agent induces a nick or double-strand break at the second recognition site; and, (ii) a second targeting vector comprising a second insert polynucleotide flanked by a third and a fourth homology arm corresponding to a third and a fourth target site located in sufficient proximity to the second recognition site; and, (b) identifying at least one cell comprising the second insert polynucleotide integrated at the target locus. In one embodiment, the nick or double-strand break at the second recognition site disrupts the activity of the second selection marker. In one embodiment, the identifying step (b) comprises culturing the cell under conditions that allow identification of cells that do not have the activity of the second selection marker. In one embodiment, the second polynucleotide comprising the second selection marker is flanked by the third target site and the fourth target site. In one embodiment, the identifying step (b) comprises identifying at least one cell comprising the second insert polynucleotide integrated at the third and the fourth target site. In one embodiment, the second insert polynucleotide comprises: (a) a second polynucleotide of interest; and, (b) a third polynucleotide encoding a third selection marker operably linked to a third promoter active in the cell, wherein the third polynucleotide comprises a third recognition site for a third nuclease agent. In one embodiment, the first nuclease agent is different from the second nuclease agent. In one embodiment, the first selection marker is different from the second selection marker. In one embodiment, the first and the third nuclease recognition site are identical to one another and are different from the second nuclease recognition site; and, the first and the third nuclease agent are identical to one another and are different from the second nuclease agent. In one embodiment, the first and the third selection markers are identical. In one embodiment, one of the first, the second or the third selection marker imparts resistance to an antibiotic. In one embodiment, the antibiotic comprises G418, hygromycin, blastocidin, neomycin, or puromycin. In one embodiment, one of the first, the second or the third selection marker is operably linked to an inducible promoter, and expression of the selection marker is toxic to the cell. In one embodiment, the first, the second or the third selection marker comprises hypoxanthine-guanine phosphoribosyltransferase (HGPRT) or thymidine kinase of Herpes simplex virus (HSV-TK). In one embodiment, said cell is a prokaryotic cell. In one embodiment, the cell is a eukaryotic cell. In one embodiment, the eukaryotic cell is a mammalian cell. In one embodiment, the mammalian cell is a non-human mammalian cell. In one embodiment, the mammalian cell is from a rodent. In one embodiment, the rodent is a rat or a mouse. In one embodiment, the mammalian cell is a human fibroblast.

In one embodiment, the cell is a pluripotent cell. In one embodiment, the mammalian cell is a human induced pluripotent stem (iPS) cell. In one embodiment, the pluripotent cell is a non-human embryonic stem (ES) cell. In one embodiment, the pluripotent cell is a mouse embryonic stem (ES) cell or a rat embryonic stem (ES) cell. In one embodiment, the pluripotent cell is a hematopoietic stem cell. In one embodiment, the pluripotent cell is a neuronal stem cell.

In one embodiment, the combined use of the first targeting vector with the first nuclease agent results in an increased targeting efficiency compared to the use of the first targeting vector alone. In one embodiment, the targeting efficiency of the first targeting vector is increased at least 2-fold compared to the use of the first targeting vector alone.

In one embodiment, the first or the second nuclease agent comprises an expression construct comprising a nucleic acid sequence encoding the nuclease agent, and the nucleic acid is operably linked to a fourth promoter active in the cell. In one embodiment, the first or the second nuclease agent is an mRNA encoding a nuclease. In one embodiment, the first or the second nuclease agent is a zinc finger nuclease (ZFN). In one embodiment, the first or the second nuclease agent is a Transcription Activator-Like Effector Nuclease (TALEN). In one embodiment, the first or the second nuclease agent is a meganuclease.

In one embodiment, the first or the second nuclease agent comprises a Clustered Regularly Interspaced Short Palindromic Repeats (CRISPR)-associated (Cas) protein and a guide RNA (gRNA). In one embodiment, the guide RNA (gRNA) comprises (a) a Clustered Regularly Interspaced Short Palindromic Repeats (CRISPR) RNA (crRNA) that targets the first, the second, or the third recognition sites; and (b) a trans-activating CRISPR RNA (tracrRNA). In one embodiment, the first or the second recognition sites are immediately flanked by a Protospacer Adjacent Motif (PAM) sequence. In one embodiment, the genomic locus of interest comprises the nucleotide sequence of SEQ ID NO: 1. In one embodiment, the Cas protein is Cas9. In one embodiment, the gRNA comprises: (a) the chimeric RNA of the nucleic acid sequence of SEQ ID NO: 2; or, (b) the chimeric RNA of the nucleic acid sequence of SEQ ID NO: 3. In one embodiment, the crRNA comprises SEQ ID NO: 4; SEQ ID NO: 5; or SEQ ID NO: 6. In one embodiment, the tracrRNA comprises SEQ ID NO: 7 or SEQ ID NO: 8. In one embodiment, the first, the second, and/or the third recognition site is located in an intron, an exon, a promoter, a promoter regulatory region, or an enhancer region of the first, the second, or the third selection marker. In one embodiment, the first target site and the second target site are immediately adjacent to the first recognition site. In one embodiment, the first target site and the second target site are about 10 nucleotides to about 14 kb from the first recognition site. In one embodiment, the third target site and the fourth target site are immediately adjacent to the second recognition site. In one embodiment, the third target site and the fourth target site are about 10 nucleotides to about 14 kb from the second recognition site. In one embodiment, a sum total of the first homology arm and the second homology arm is at least about 10 kb. In one embodiment, a sum total of the third homology arm and the fourth homology arm is at least about 10 kb. In one embodiment, the first insert polynucleotide ranges from about 5 kb to about 300 kb in length. In one embodiment, the second insert polynucleotide ranges from about 5 kb to about 300 kb in length. In one embodiment, integration of the first insert polynucleotide into the target locus results in a knockout, a knock-in, a point mutation, a domain swap, an exon swap, an intron swap, a regulatory sequence swap, a gene swap, or a combination thereof. In one embodiment, integration of the second insert polynucleotide into the target locus results in a knockout, a knock-in, a point mutation, a domain swap, an exon swap, an intron swap, a regulatory sequence swap, a gene swap, or a combination thereof. In one embodiment, the first insert polynucleotide comprises a polynucleotide of interest comprising a human polynucleotide. In one embodiment, the second insert polynucleotide comprises a polynucleotide of interest comprising a human polynucleotide. In one embodiment, the first insert polynucleotide comprises a polynucleotide of interest comprising a region of the T cell receptor alpha locus. In one embodiment, the second insert polynucleotide comprises a polynucleotide of interest comprising a region of the T cell receptor alpha locus. In one embodiment, the first or the second insert polynucleotide comprises a polynucleotide of interest comprising at least one variable region gene segment and/or a joining region gene segment of the T cell receptor alpha locus. In one embodiment, the region of the T cell receptor alpha locus is from a human. In one embodiment, the first insert polynucleotide comprises a polynucleotide of interest comprising an unrearranged human immunoglobulin heavy chain variable region nucleic acid sequence operably linked to a non-human immunoglobulin heavy chain constant region nucleic acid sequence. In one embodiment, the identifying step is carried out via a modification of allele (MOA) assay. In one embodiment, wherein the first insert polynucleotide comprises a polynucleotide of interest comprising a nucleic acid sequence that is homologous or orthologous to the nucleic acid sequence in a genome of the cell. In one embodiment, the second insert polynucleotide comprises a nucleic acid sequence that is homologous or orthologous to the nucleic acid sequence in a genome of the cell. In one embodiment, the first insert polynucleotide comprises a polynucleotide of interest comprising an exogenous nucleic acid sequence. In one embodiment, the second insert polynucleotide comprises a polynucleotide of interest comprising an exogenous nucleic acid sequence.

DETAILED DESCRIPTION

Figure 1:
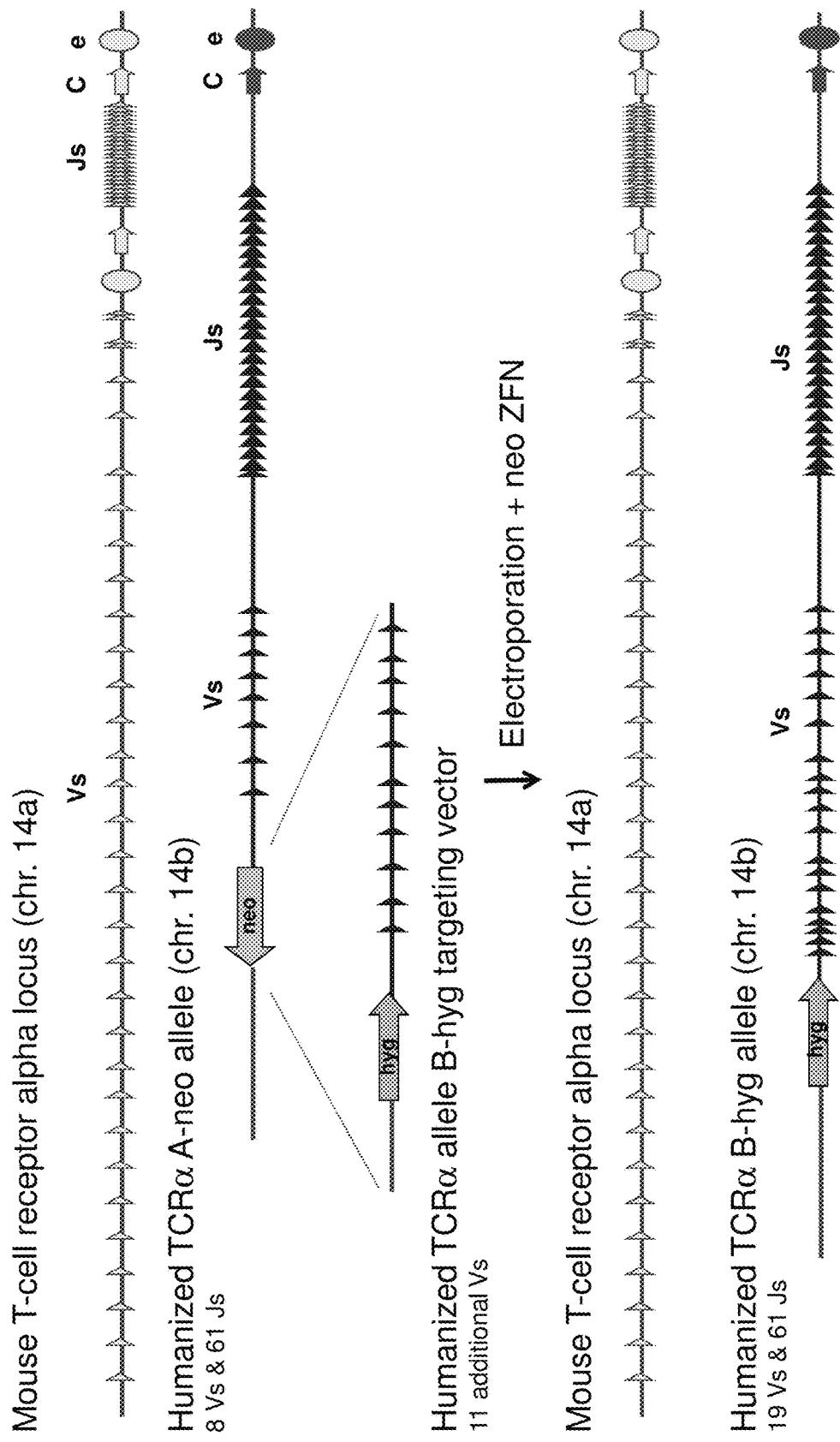
FIG. 1 provides a schematic for a genomic targeting event in which a cell having a heterozygous modification of the TCR alpha locus on mouse chromosome 14, one allele of which is the humanized TCR alpha A-neo allele, comprising a neomycin selection cassette located upstream of eight human variable (V) gene segments and 61 human joining (J) gene segments is targeted with a humanized TCR alpha allele B-hyg targeting vector, comprising a hygromycin selection cassette and a fragment of greater than 100 kb comprising 11 additional human variable gene segments. Electroporation of the allele B-hyg targeting vector and plasmids expressing the two halves of a zinc finger nuclease (ZFN) pair that targets the neomycin cassette in the TCR alpha A-neo allele generated a modified TCR alpha locus (allele B-hyg) comprising, from 5' to 3', a hygromycin cassette, 19 human V gene segments, and 61 human J gene segments located upstream of the endogenous constant region nucleotide sequence. The targeting event precisely inserted more than 100 kb of human TCR alpha gene sequence into the mouse TCR alpha locus.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are included within the scope of the appended claims. Although specific terms are employed herein, they are used in a generic and descriptive sense only and not for purposes of limitation.

I. Overview

Methods and compositions are provided for modifying a target locus, e.g., genomic locus, in a cell. The methods and compositions employ nuclease agents and nuclease agent recognition sites to enhance homologous recombination events of an insert polynucleotide into the target locus. The various methods and compositions provided herein strategically locate the nuclease agent recognition site within a polynucleotide encoding a selection marker, a reporter, or an exogenous protein (e.g., eGFP or a human sequence in a mouse cell).

Further provided are methods that allow for the serial modification (i.e., tiling) of polynucleotides of interest at a target locus (i.e., a genomic locus). As explained in further detail below, methods are provided to serially tile polynucleotides of interest in a target locus (i.e., a genomic locus) wherein the target locus (i.e., a genomic locus) and the various targeting vectors employed in the method alternate the use of a first selection marker comprising a first recognition site for a first nuclease agent and a second selection marker comprising a second recognition site for a second nuclease agent. In doing so, the method does not require a constant supply of nucleases engineered to recognize new recognition sites. Instead, in specific embodiments, the targeted serial tiling only requires two nuclease agents and the corresponding recognition site of the two nuclease agents. Moreover, since the nuclease agents target exogenous sequences (i.e., the recognition site within a polynucleotide encoding a selection marker) and since the efficacy and off-target effect of any given recognition site will have been previously confirmed, non-specific cleavage of an endogenous genomic sequence can be minimized while increasing the time and cost efficiency of the tiling process.

II. Targeted Integration System

Methods and compositions are provided for modifying a target locus in a cell. The system employs nuclease agents, recognition sites for the nuclease agent, a target locus, selection markers, targeting vectors, and insert polynucleotides. Each of these components is described in further detail below.

A. Nuclease Agents and Recognition Sites for Nuclease Agents

The term "recognition site for a nuclease agent" includes a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desires to be positioned at the target locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary, and includes, for example, recognition sites that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break into a desired recognition site can be used in the methods and compositions disclosed herein. A naturally occurring or native nuclease agent can be employed so long as the nuclease agent induces a nick or double-strand break in a desired recognition site. Alternatively, a modified or engineered nuclease agent can be employed. An "engineered nuclease agent" includes a nuclease that is engineered (modified or derived) from its native form to specifically recognize and induce a nick or double-strand break in the desired recognition site. Thus, an engineered nuclease agent can be derived from a native naturally occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art (e.g., TaqMan® qPCR assay, Frendewey D. et al., Methods in Enzymology, 2010, 476: 295-307, which is incorporated by reference herein in its entirety).

In specific embodiments, the recognition site is positioned within the polynucleotide encoding the selection marker. Such a position can be located within the coding region of the selection marker or within the regulatory regions, which influence the expression of the selection marker. Thus, a recognition site of the nuclease agent can be located in an intron of the selection marker, a promoter, an enhancer, a regulatory region, or any non-protein-coding region of the polynucleotide encoding the selection marker. In specific embodiments, a nick or double-strand break at the recognition site disrupts the activity of the selection marker. Methods to assay for the presence or absence of a functional selection marker are known.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res.* (2010) doi:10.1093/nar/gkq704; and Miller et al. (2011) *Nature Biotechnology* 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 33-35 TAL repeats that recognize a single base pair via two hypervariable residues. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease subunit, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, for example, US20060246567; US20080182332; US20020081614; US20030021776; WO/2002/057308A2; US20130123484; US20100291048; WO/2011/017293A2; and Gaj et al. (2013) *Trends in Biotechnology*, 31(7):397-405, each of which is herein incorporated by reference.

In still another embodiment, the nuclease agent is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long recognition sites, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-DmoI.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.).

The nuclease agent employed in the various methods and compositions can also comprise a CRISPR/Cas system. Such systems can employ a Cas9 nuclease, which in some instances, is codon-optimized for the desired cell type in which it is to be expressed. The system further employs a fused crRNA-tracrRNA construct that functions with the codon-optimized Cas9. This single RNA is often referred to as a guide RNA or gRNA. Within a gRNA, the crRNA portion is identified as the 'target sequences' for the given recognition site and the tracrRNA is often referred to as the 'scaffold'. This system has been shown to function in a variety of eukaryotic and prokaryotic cells. Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. The gRNA expression cassette and the Cas9 expression cassette are then introduced into the cell. See, for example, Mali P et al. (2013) *Science* 2013 Feb. 15; 339 (6121):823-6; Jinek M et al. *Science* 2012 Aug. 17; 337 (6096):816-21; Hwang W Y et al. *Nat Biotechnol* 2013 March; 31(3):227-9; Jiang W et al. *Nat Biotechnol* 2013 March; 31(3):233-9; and, Cong L et al. *Science* 2013 Feb. 15; 339(6121):819-23, each of which is herein incorporated by reference.

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

i. Cas RNA-Guided Endonucleases

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Cas proteins can be from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina,*

*Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Additional examples of the Cas9 family members are described in WO 2014/131833, herein incorporated by reference in its entirety. Cas9 protein from *S. pyogenes* or derived therefrom is a preferred enzyme. Cas9 protein from *S. pyogenes* is assigned SwissProt accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, hereby incorporated by reference in its entirety.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a CRISPR RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA. An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety. Such mutations can be generated using methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference.

Cas proteins can also be fusion proteins. For example, a Cas protein can be fused to a cleavage domain, an epigenetic modification domain, a transcriptional activation domain, or a transcriptional repressor domain. See WO 2014/089290, incorporated herein by reference in its entirety. Cas proteins can also be fused to a heterologous polypeptide providing increased or decreased stability. The fused domain or heterologous polypeptide can be located at the N-terminus, the C-terminus, or internally within the Cas protein.

A Cas protein can be fused to a heterologous polypeptide that provides for subcellular localization. Such heterologous peptides include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. Promoters that can be used in an expression construct include, for example, promoters active in a pluripotent rat, eukaryotic, mammalian, non-human mammalian, human, rodent, mouse, or hamster cell. Examples of other promoters are described elsewhere herein.

ii. Guide RNAs (gRNAs)

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference. The terms "guide RNA" and "gRNA" include both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, for example, Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of *S. pyogenes*, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (i.e., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from *S. pyogenes* include 171-nucleotide, 89-nucleotide, 75-nucleotide, and 65-nucleotide versions. See, for example, Deltcheva et al. (2011) *Nature* 471:602-607; WO 2014/093661, each of which is incorporated herein by reference in their entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, incorporated herein by reference in its entirety.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the CRISPR RNA recognition sequence within the target DNA can be at least 60% over about 20 contiguous nucleotides. As an example, the percent complementarity between the DNA-targeting sequence and the CRISPR RNA recognition sequence within the target DNA is 100% over the 14 contiguous nucleotides at the 5' end of the CRISPR RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the CRISPR RNA recognition sequence within the target DNA is 100% over the seven contiguous nucleotides at the 5' end of the CRISPR RNA recognition sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the RNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively.

DNAs encoding gRNAs can be stably integrated in the genome of the cell and operably linked to a promoter active in the cell. Alternatively, DNAs encoding gRNAs can be operably linked to a promoter in an expression construct. Such promoters can be active, for example, in a pluripotent rat, eukaryotic, mammalian, non-human mammalian, human, rodent, mouse, or hamster cell. In some instances, the promoter is an RNA polymerase III promoter, such as a human U6 promoter, a rat U6 polymerase III promoter, or a mouse U6 polymerase III promoter. Examples of other promoters are described elsewhere herein.

Alternatively, gRNAs can be prepared by various other methods. For example, gRNAs can be prepared by in vitro transcription using, for example, T7 RNA polymerase (see, for example, WO 2014/089290 and WO 2014/065596). Guide RNAs can also be a synthetically produced molecule prepared by chemical synthesis.

iii. CRISPR RNA Recognition Sequences

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell, such as a mitochondrion or chloroplast.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the CRISPR RNA recognition sequence of the non-complementary strand of the target DNA. As such, the PAM sequence of the complementary strand would be 5'-CC$N_2$-3', where $N_2$ is any DNA nucleotide and is immediately 5' of the CRISPR RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T, $N_1$=T, and $N_2$=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein (see, for example, WO 2014/165825). The guanine at the 5' end can facilitate transcription by RNA polymerase in cells. Other examples of CRISPR RNA recognition sequences can include two guanine nucleotides at the 5' end (e.g., GG$N_{20}$NGG; SEQ ID NO: 21) to facilitate efficient transcription by T7 polymerase in vitro. See, for example, WO 2014/065596.

The CRISPR RNA recognition sequence can be any nucleic acid sequence endogenous or exogenous to a cell. The CRISPR RNA recognition sequence can be a sequence coding a gene product (e.g., a protein) or a non-coding sequence (e.g., a regulatory sequence) or can include both. In one embodiment, the target sequence is immediately flanked by a Protospacer Adjacent Motif (PAM) sequence. In one embodiment, the locus of interest comprises the nucleotide sequence of SEQ ID NO: 1. In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA). In another embodiment, the genome of the pluripotent rat cell comprises a target DNA region complementary to the target sequence. In some such methods, the Cas protein is Cas9. In some embodiments, the gRNA comprises (a) the chimeric RNA of the nucleic acid sequence of SEQ ID NO: 2; or (b) the chimeric RNA of the nucleic acid sequence of SEQ ID NO: 3. In some such methods, the crRNA comprises the sequence set forth in SEQ ID NO: 4, SEQ ID NO: 5, or SEQ ID NO: 6. In some such methods, the tracrRNA comprises the sequence set forth in SEQ ID NO: 7 or SEQ ID NO: 8.

Active variants and fragments of nuclease agents (i.e. an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

Figure 3:
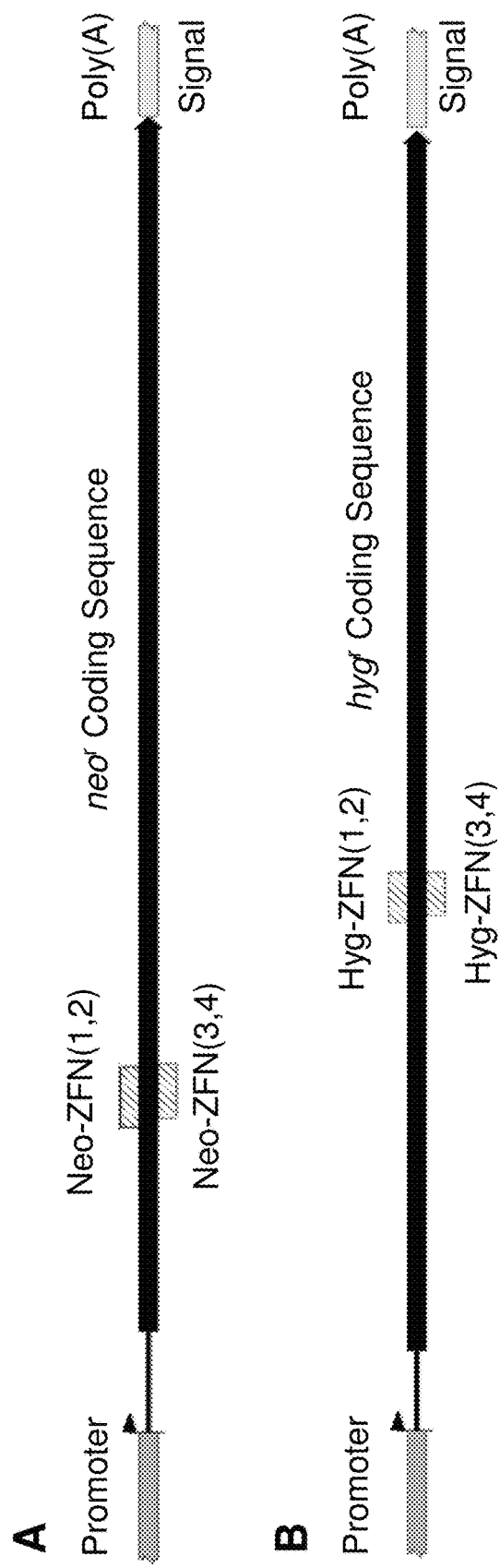
FIG. 3 provides a schematic representation of the neo$^r$, encoding neomycin phosphotransferase, and hyg$^r$, encoding hygromycin B phosphotransferase, drug selection cassettes. The positions of the recognition sites (sequences given below) for the Neo-ZFN(1,2) and Neo-ZFN(3,4) zinc finger nucleases (ZFNs, FIG. 3A) that target neo$^r$ and the Hyg-ZFN(1,2) and Hyg-ZFN(3,4) ZFNs (FIG. 3B) that target hyg$^r$ are indicated by hatched boxes above or below to the thick arrows representing the respective phosphotransferase coding sequences.

For example, FIG. 3 depicts the positions of the ZFN binding sites and cut sites on the selection cassettes. The sites are as follows: Neo-ZFN(1,2): NUCLEASE BINDING SITE/cutsite GGGCGCCCGGTTCTTTTT/gtcaag/ACCGACCTGTCCGGTG (SEQ ID NO: 9); Neo-ZFN(3,4): NUCLEASE BINDING SITE/cutsite CCGGTTCTTTTTGTC/aagacc/GACCTGTCCGGTGCC (SEQ ID NO: 10); Hyg-ZFN(1,2): NUCLEASE BINDING SITE/cutsite TGCGATCGCTGCGGCCGA/tcttag/CCAGACGAGCGGGTTCGG (SEQ ID NO: 11); and, Hyg-ZFN(3,4): NUCLEASE BINDING SITE/cutsite CGCTGCGGCCGATCT/tagcca/GACGAGCGGGTTCGG (SEQ ID NO: 12).

The nuclease agent may be introduced into the cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally or constitutive expressed within the cell. Thus, the polynucleotide encoding the nuclease agent can be contained in an expression cassette and be operably linked to a conditional promoter, an inducible promoter, a constitutive promoter, or a tissue-specific promoter. Such promoters of interest are discussed in further detail elsewhere herein. Alternatively, the nuclease agent is introduced into the cell as an mRNA encoding a nuclease agent.

In specific embodiments, the polynucleotide encoding the nuclease agent is stably integrated in the genome of the cell and operably linked to a promoter active in the cell. In other embodiments, the polynucleotide encoding the nuclease agent is in the same targeting vector comprising the insert polynucleotide, while in other instances the polynucleotide encoding the nuclease agent is in a vector or a plasmid that is separate from the targeting vector comprising the insert polynucleotide.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

B. Selection Markers

The various methods and compositions provided herein employ the nuclease agents and their corresponding recognition sites in combination with selection markers. As discussed herein, the position of the recognition site in the polynucleotide encoding the selection marker allows for an efficient method by which to identify integration events at the target locus. Moreover, various methods are provided herein wherein alternating selection markers having the nuclease recognition site are employed to improve the efficiency and efficacy through which multiple polynucleotides of interest are integrated within a given targeted locus.

Various selection markers can be used in the methods and compositions disclosed herein. Such selection markers can, for example, impart resistance to an antibiotic such as G418, hygromycin, blastocidin, neomycin, or puromycin. Such selection markers include neomycin phosphotransferase (neo$^r$), hygromycin b phosphotransferase (hyg$^r$), puromycin-n-acetyltransferase (puro$^r$), and blasticidin s deaminase (bsr$^r$). In still other embodiments, the selection marker is operably linked to an inducible promoter and the expression of the selection marker is toxic to the cell. Non-limiting examples of such selection markers include xanthine/guanine phosphoribosyl transferase (gpt), hypoxanthine-guanine phosphoribosyltransferase (HGPRT) or herpes simplex virus thymidine kinase (HSV-TK).

The polynucleotide encoding the selection markers are operably linked to a promoter active in the cell. Such expression cassettes and their various regulatory components are discussed in further detailed elsewhere herein.

C. Target Locus

Various methods and compositions are provided, which allow for the integration of at least one insert polynucleotide at a target locus. The term "target locus" comprises any segment or region of DNA that one desires to integrate an insert polynucleotide. In one embodiment, the target locus is a genomic locus. The target locus can be native to the cell, or alternatively can comprise a heterologous or exogenous segment of DNA. Such heterologous or exogenous segments of DNA can include transgenes, expression cassettes, polynucleotide encoding selection makers, or heterologous or exogenous regions of DNA (i.e., heterologous or exogenous regions of genomic DNA). The target locus can comprise any of the targeted integration system including, for example, the recognition site, the selection marker, previously integrated insert polynucleotides, polynucleotides encoding nuclease agents, promoters, etc. Alternatively, the target locus can be located within a yeast artificial chromosome (YAC), bacterial artificial chromosome (BAC), a human artificial chromosome, or any other engineered genomic region contained in an appropriate host cell. Thus, in specific embodiments, the targeted locus can comprise native, heterologous or exogenous genomic nucleic acid sequence from a prokaryote, a eukaryote, yeast, bacteria, a non-human mammal, a non-human cell, a rodent, a human, a rat, a mouse, a hamster, a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest or a combination thereof.

Non-limiting examples of the target locus include, a genomic locus that encodes a protein expressed in a B cell, a genomic locus that expresses a polypeptide in an immature B cell, a genomic locus that expresses a polypeptide in a mature B cell, an immunoglobulin (Ig) loci, or a T cell receptor loci, including for example a T cell receptor alpha locus. Such locus can be from a bird (e.g., a chicken), a non-human mammal, a rodent, a human, a rat, a mouse, a hamster, a rabbit, a pig, a bovine, a deer, a sheep, a goat, a cat, a dog, a ferret, a primate (e.g., marmoset, rhesus monkey), domesticated mammal or an agricultural mammal or any other organism of interest or a combination thereof.

In further embodiments, the targeted locus is not targetable using a conventional method or can be targeted only incorrectly or only with significantly low efficiency, in the absence of a nick or double-strand break induced by a nuclease agent.

D. Targeting Vectors and Insert Polynucleotides

As outlined above, the methods and compositions provided herein take advantage of nuclease agents and the strategic positioning of recognition sites for a nuclease agent within a selection cassette in combination with a homologous recombination event. Such methods employ the nick or double-strand break at the recognition site in combination with homologous recombination to thereby target the integration of an insert polynucleotide into the target locus. "Homologous recombination" is used conventionally to include the exchange of DNA fragments between two DNA molecules at cross-over sites within the regions of homology.

i. Insert Polynucleotide

The term "insert polynucleotide" comprises a segment of DNA that one desires to integrate at the target locus. In one embodiment, the insert polynucleotide comprises one or more polynucleotides of interest. In other embodiments, the insert polynucleotide can comprise one or more expression cassettes. A given expression cassette can comprise a polynucleotide of interest, a polynucleotide encoding a selection marker and/or a reporter gene along with the various regulatory components that influence expression. Non-limiting examples of polynucleotides of interest, selection markers, and reporter genes (e.g., eGFP) that can be included within the insert polynucleotide are discussed in detail elsewhere herein.

In specific embodiments, the insert polynucleotide can comprise a genomic nucleic acid. In one embodiment, the genomic nucleic acid is derived from a mouse, a human, a rodent, a non-human, a rat, a hamster, a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest or a combination thereof.

In further embodiments, the insert polynucleotide comprises a conditional allele. In one embodiment, the conditional allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

The insert polynucleotide can be from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

In specific embodiments, the insert polynucleotide comprises a nucleic acid flanked with site-specific recombination target sequences. It is recognized that while the entire insert polynucleotide can be flanked by such site-specific recombination target sequence, any region or individual polynucleotide of interest within the insert polynucleotide can also be flanked by such sites. The term "recombination site" includes a nucleotide sequence that is recognized by a site-specific recombinase and that can serve as a substrate for a recombination event. The term "site-specific recombinase" includes a group of enzymes that can facilitate recombination between recombination sites where the two recombination sites are physically separated within a single nucleic acid molecule or on separate nucleic acid molecules. Examples of site-specific recombinases include, but are not limited to, Cre, Flp, and Dre recombinases. The site-specific recombinase can be introduced into the cell by any means, including by introducing the recombinase polypeptide into the cell or by introducing a polynucleotide encoding the site-specific recombinase into the host cell. The polynucleotide encoding the site-specific recombinase can be located within the insert polynucleotide or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences which can flank the insert polynucleotide or any polynucleotide of interest in the insert polynucleotide can include, but are not limited to, loxP, lox511, lox2272, lox66, lox71, loxM2, lox5171, FRT, FRT11, FRT71, attp, att, FRT, rox, and a combination thereof.

In other embodiments, the site-specific recombination sites flank a polynucleotide encoding a selection marker and/or a reporter gene contained within the insert polynucleotide. In such instances following integration of the insert polynucleotide at the targeted locus the sequences between the site-specific recombination sites can be removed.

In one embodiment, the insert polynucleotide comprises a polynucleotide encoding a selection marker. Such selection markers include, but are not limited, to neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. In one embodiment, the polynucleotide encoding the selection marker is operably linked to a promoter active in the cell. When serially tiling polynucleotides of interest into a targeted locus (i.e., a genomic locus), the selection marker can comprise a recognition site for a nuclease agent, as outlined above. In one embodiment, the polynucleotide encoding the selection marker is flanked with a site-specific recombination target sequences.

The insert polynucleotide can further comprise a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. Such reporter genes can be operably linked to a promoter active in the cell. Such promoters can be an inducible promoter, a promoter that is endogenous to the reporter gene or the cell, a promoter that is heterologous to the reporter gene or to the cell, a cell-specific promoter, a tissue-specific promoter manner or a developmental stage-specific promoter.

ii. Targeting Vectors

Targeting vectors are employed to introduce the insert polynucleotide into the targeted locus. The targeting vector comprises the insert polynucleotide and further comprises an upstream and a downstream homology arm, which flank the insert polynucleotide. The homology arms, which flank the insert polynucleotide, correspond to regions within the targeted locus. For ease of reference, the corresponding regions within the targeted locus are referred to herein as "target sites". Thus, in one example, a targeting vector can comprise a first insert polynucleotide flanked by a first and a second homology arm corresponding to a first and a second target site located in sufficient proximity to the first recognition site within the polynucleotide encoding the selection marker. As such, the targeting vector thereby aids in the integration of the insert polynucleotide into the targeted locus through a homologous recombination event that occurs between the homology arms and the corresponding target sites, for example, within the genome of the cell.

A homology arm of the targeting vector can be of any length that is sufficient to promote a homologous recombination event with a corresponding target site, including for example, 50-100 bases, 100-1000 bases or at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 100-200, or 200-300 kilobases in length or greater. As outlined in further detail below, large targeting vectors can employ targeting arms of greater length.

The target sites within the targeted locus that correspond to the upstream and downstream homology arms of the targeting vector are located in "sufficient proximity to the recognition site" located in the polynucleotide encoding the selection marker. The upstream and downstream homology arms of a targeting vector are "located in sufficient proximity" to a recognition site where the distance is such as to promote the occurrence of a homologous recombination event between the target sites and the homology arms upon a nick or double-strand break at the recognition site. Thus, in specific embodiments, the target sites corresponding to the upstream and/or downstream homology arm of the targeting vector are within at least 1 nucleotide of a given recognition site, are within at least 10 nucleotides to about 14 kb of a given recognition site or are within about 10 nucleotides to about 100 nucleotides, about 100 nucleotides to about 500 nucleotides, about 500 nucleotides to about 1000 nucleotides, about 1 kb to about 5 kb, about 5 kb to about 10 kb, or about 10 kb to about 14 kb of a given recognition site. In specific embodiments, the recognition site is immediately adjacent to at least one or both of the target sites.

The spatial relationship of the target sites that correspond to the homology arms of the targeting vector and the recognition site within the polynucleotide encoding the selection marker can vary. For example, target sites can be located 5' to the recognition site, both target sites can be located 3' to the recognition site, or the target sites can flank the recognition site.

A homology arm and a target site "correspond" or are "corresponding" to one another when the two regions share a sufficient level of sequence identity to one another to act as substrates for a homologous recombination reaction. By "homology" is meant DNA sequences that are either identical or share sequence identity to a corresponding sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target site can be of any length that is sufficient to promote homologous recombination at the cleaved recognition site. For example, a given homology arm and/or corresponding target site can comprise corresponding regions of homology that are at least about 50-100 bases, 100-1000 bases, or 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 100-200, or 200-300 kilobases in length or more (such as described in the LTVEC vectors described elsewhere herein) such that the homology arm has sufficient homology to undergo homologous recombination with the corresponding target sites within the genome of the cell.

For ease of reference the homology arms include an upstream and a downstream homology arm. This terminology relates to the relative position of the homology arms to the insert polynucleotide within the targeting vector.

The homology arms of the targeting vector are therefore designed to correspond to a target site with the targeted locus. Thus, the homology arms can correspond to a locus that is native to the cell, or alternatively they can correspond to a region of a heterologous or exogenous segment of DNA that was integrated into the genome of the cell, including, but not limited to, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further the homology arms of the targeting vector can correspond to or be derived from a region of a BAC library, a cosmid library, or a P1 phage library. Thus, in specific embodiments, the homology arms of the targeting vector correspond to a locus that is native, heterologous or exogenous to a prokaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), domesticated mammal or an agricultural mammal or any other organism of interest. In further embodiments, the homology arms correspond to a locus of the cell that is not targetable using a conventional method or can be targeted only incorrectly or only with significantly low efficiency, in the absence of a nick or double-strand break induced by a nuclease agent. In one embodiment, the homology arms are derived from a synthetic DNA.

In still other embodiments, the upstream and downstream homology arms correspond to the same genome as the targeted genome. In one embodiment, the homology arms are from a related genome, e.g., the targeted genome is a mouse genome of a first strain, and the targeting arms are from a mouse genome of a second strain, wherein the first strain and the second strain are different. In other embodiments, the homology arms are from the genome of the same animal or are from the genome of the same strain, e.g., the targeted genome is a mouse genome of a first strain, and the targeting arms are from a mouse genome from the same mouse or from the same strain.

The targeting vector (such as a large targeting vector) can also comprise a selection cassette or a reporter gene as discussed elsewhere herein. The selection cassette can comprise a nucleic acid sequence encoding a selection marker, wherein the nucleic acid sequence is operably linked to a promoter. The promoter can be active in a prokaryotic cell of interest and/or active in a eukaryotic cell of interest. Such promoters can be an inducible promoter, a promoter that is endogenous to the reporter gene or the cell, a promoter that is heterologous to the reporter gene or to the cell, a cell-specific promoter, a tissue-specific promoter or a developmental stage-specific promoter. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof. The selection marker of the targeting vector can be flanked by the upstream and downstream homology arms or found either 5' or 3' to the homology arms.

In one embodiment, the targeting vector (such as a large targeting vector) comprises a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. Such reporter genes can be operably linked to a promoter active in the cell. Such promoters can be an inducible promoter, a promoter that is endogenous to the report gene or the cell, a promoter that is heterologous to the reporter gene or to the cell, a cell-specific promoter, a tissue-specific promoter manner or a developmental stage-specific promoter.

In one embodiment, combined use of the targeting vector (including, for example, a large targeting vector) with the nuclease agent results in an increased targeting efficiency compared to use of the targeting vector alone. In one embodiment, when the targeting vector is used in conjunction with the nuclease agent, targeting efficiency of the targeting vector is increased at least by two-fold, at least three-fold, at least 4-fold, or at least 10-fold when compared to when the targeting vector is used alone.

iii. Large Targeting Vectors

The term "large targeting vector" or "LTVEC" includes large targeting vectors that comprise homology arms that correspond to and are derived from nucleic acid sequences larger than those typically used by other approaches intended to perform homologous recombination in cells and/or comprising insert polynucleotides comprising nucleic acid sequences larger than those typically used by other approaches intended to perform homologous recombination in cells. In specific embodiments, the homology arms and/or the insert polynucleotide of the LTVEC comprises genomic sequence of a eukaryotic cell. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC), a human artificial chromosome or a yeast artificial chromosome (YAC). Non-limiting examples of LTVECs and methods for making them are described, e.g., in U.S. Pat. Nos. 6,586,251, 6,596,541, 7,105,348, and WO 2002/036789 (PCT/US01/45375), each of which is herein incorporated by reference.

The LTVEC can be of any length, including, but not limited to, from about 20 kb to about 300 kb, from about 20 kb to about 30 kb, from about 30 kb to about 40 kb, from about 40 kb to about 50 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb.

In one embodiment, the LTVEC comprises an insert polynucleotide ranging from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

In one embodiment, the homology arms of the LTVEC are derived from a BAC library, a cosmid library, or a P1 phage library. In other embodiments, the homology arms are derived from the targeted locus (i.e., genomic locus) of the cell and in some instances the target locus, which the LTVEC is designed to target is not targetable using a conventional method. In still other embodiments, the homology arms are derived from a synthetic DNA. In one embodiment, a sum total of the upstream homology arm and the downstream homology arm in the LTVEC is at least 10 kb. In one embodiment, the upstream homology arm ranges from about 1 kb to about 100 kb. In other embodiments, the upstream homology arm ranges from about 5 kb to about 100 kb. In one embodiment, the downstream homology arm ranges from about 1 kb to about 100 kb. In one embodiment, the downstream homology arm ranges from about 5 kb to about 100 kb. In other embodiments, the sum total of the upstream and downstream homology arms are from about 1 kb to about 5 kb, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

In other embodiments, sum total of the 5' and the 3' homology arms of the LTVEC is from about 10 kb to about 30 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb. In other instances, the sum total of the 5' and 3' homology arm is about 16 Kb to about 150 Kb.

In further embodiments, the LTVEC and insert polynucleotide is designed so as to allow for a deletion at the target locus from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In other instances, the LTVEC and insert polynucleotide is designed so as to allow for an insertion into the target locus of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. In one embodiment, the insert polynucleotide is about 130 kb or about 155 kb.

In one embodiment, the LTVEC comprises a selection cassette or a reporter gene as discussed elsewhere herein.

III. Methods for Integrating a Polynucleotide of Interest into a Target Locus

A. Methods of Integration of an Insert Polynucleotide Near the Recognition Site by Homologous Recombination Methods for modifying a target locus in a cell are provided. The methods comprise (a) providing a cell comprising a first polynucleotide encoding a first selection marker operably linked to a first promoter active in the cell, wherein the first polynucleotide further comprising a first recognition site for a first nuclease agent; (b) introducing into the cell: (i) a first nuclease agent that induces a nick or double-strand break at the first recognition site, and, (ii) a first targeting vector comprising a first insert polynucleotide flanked by a first and a second homology arm that correspond to a first and a second target site located in sufficient proximity to the first recognition site; and, (c) identifying at least one cell comprising the first insert polynucleotide integrated at the target locus. In specific embodiments, the first polynucleotide comprising the first selection marker is flanked by a first target site and a second target site, the first target site corresponds to the first homology arm in the first targeting vector and the second target site corresponds to the second homology arm in the first targeting vector.

Various methods can be used to identify cells having the insert polynucleotide integrated at the target locus. In one embodiment, the nick or double-strand break at the first recognition site disrupts the activity of the first selection marker. Thus, in one embodiment, such cells are identified by culturing the cells under conditions that identify cells, which do not have the activity of the selection marker encoded by the polynucleotide having the recognition site, which was cut by the nuclease agent. Methods that employ such selection markers and assaying for their activity are known. Additional method for identifying cells having the insert polynucleotide at the target locus can comprise identifying at least one cell comprising having the insert polynucleotide integrated at the desired target site. Such methods can include identifying at least one cell comprising in its genome the first insert polynucleotide integrated at the first and the second target site.

Additional methods can also be employed to identify cells having the insert polynucleotide integrated at the target locus. Insertion of the insert polynucleotide at the target locus results in a "modification of allele." The term "modification of allele" or "MOA" includes the modification of the exact DNA sequence of one allele of a gene(s) or chromosomal locus (loci) in a genome. Examples of "modification of allele (MOA)" include, but are not limited to, deletions, substitutions, or insertions of as little as a single nucleotide or deletions of many kilobases spanning a gene(s) or chromosomal locus (loci) of interest, as well as any and all possible modifications between these two extremes.

In various embodiments, to facilitate identification of the targeted modification, a high-throughput quantitative assay, namely, modification of allele (MOA) assay, is employed. The MOA assay described herein allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer set that recognizes the target locus and a second primer set that recognizes a non-targeted reference locus. In addition, the primer set comprises a fluorescent probe that recognizes the amplified sequence. The quantitative assay can also be carried out via a variety of analytical techniques, including, but not limited to, fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, and Eclipse™ probe technology. (See, for example, US2005/0144655, incorporated by reference herein in its entirety).

The presence of a nick or a double-strand break in the recognition site within the selection marker, in various embodiments, increases the efficiency and/or frequency of recombination between a targeting vector (such as an LTVEC) and the targeted locus. In one embodiment the recombination is homologous recombination. In various embodiments, in the presence of the nick or double strand bread, targeting efficiency of a targeting vector (such as a LTVEC) at the target locus is at least about 2-fold higher, at least about 3-fold higher, at least about 4-fold, at least about 10-fold higher than in the absence of the nick or double-strand break (using, e.g., the same targeting vector and the same homology arms and corresponding target sites at the locus of interest but in the absence of an added nuclease agent that makes the nick or double strand break).

B. Methods of Integrating Multiple Polynucleotides of Interest at the Targeted Locus The various methods and compositions provided herein allow for the targeted integration of multiple polynucleotides of interest within a given target locus. The methods employ the targeted integration system described herein, which employs strategic positioning of the nuclease agent recognition site within a polynucleotide encoding selection marker. In specific embodiments, the selection marker and the recognition site is alternated within each insert polynucleotide. In doing so, the tiling of sequential insert polynucleotides within a given target locus occurs with an enhanced efficiency and efficacy.

In one embodiment, the method for modifying a target locus in a cell comprises: (a) providing a cell comprising a locus that comprises a first polynucleotide encoding a first selection marker operably linked to a first promoter active in the cell, wherein the first polynucleotide further comprises a first recognition site for a first nuclease agent; (b) introducing into the cell a first nuclease agent, wherein the first nuclease agent induces a nick or double-strand break at the first recognition site; and, introducing into the cell a first targeting vector comprising a first insert polynucleotide flanked by a first and a second homology arm, which correspond to a first and a second target site located in sufficient proximity to the first recognition site; and the first insert polynucleotide further comprises (1) a first polynucleotide of interest; and, (2) a second polynucleotide encoding a second selection marker operably linked to a second promoter active in the cell, wherein the second polynucleotide comprises a second recognition site for a second nuclease agent; and, (c) identifying at least one cell comprising the first insert polynucleotide integrated at the target locus.

In further embodiments, additional polynucleotides of interest can be integrated at the target locus. Such methods for modifying a target locus in a cell comprise: (a) providing a cell comprising a locus, which comprises a first polynucleotide encoding a first selection marker operably linked to a first promoter active in the cell, wherein the first polynucleotide further comprises a first recognition site for a first nuclease agent; (b) introducing into the cell a first nuclease agent, wherein the first nuclease agent induces a nick or double-strand break at the first recognition site; and, introducing into the cell a first targeting vector comprising a first insert polynucleotide flanked by a first and a second homology arm, which correspond to a first and a second target site located in sufficient proximity to the first recognition site; and the first insert polynucleotide further comprises (1) a first polynucleotide of interest; and, (2) a second polynucleotide encoding a second selection marker operably linked to a second promoter active in the cell, wherein the second polynucleotide comprises a second recognition site for a second nuclease agent; (c) identifying at least one cell comprising the first insert polynucleotide integrated at the target locus; (d) introducing into the cell comprising in its genome the first insert polynucleotide integrated at the target locus, (i) a second nuclease agent, wherein the second nuclease agent induces a nick or double-strand break at the second recognition site; and, (ii) a second targeting vector comprising a second insert polynucleotide flanked by a third and a fourth homology arm; and, (b) identifying at least one cell comprising the second insert polynucleotide integrated at the target locus. In specific embodiments, the nick or double-strand break at the second recognition maker disrupts the activity of the second selection marker. In further embodiments, identifying at least one cell comprising the second insert polynucleotide integrated at the target locus comprises culturing the cell under conditions that identify cells which do not have the activity of the second selection marker. In still further embodiments, the second polynucleotide comprising the second selection marker is flanked by a third target site and a fourth target site, the third target site corresponds to the third homology arm in the second targeting vector and the fourth target site corresponds to the fourth homology arm in the second targeting vector. In still further embodiments, identifying at least one cell comprising the second insert polynucleotide integrated at the target locus comprises identifying at least one cell comprising the second insert polynucleotide integrated at the third and the fourth target site.

Additional methods for modifying a target locus in a cell comprise: (a) providing a cell comprising a target locus comprising a first polynucleotide encoding a first selection marker operably linked to a first promoter active in the cell, wherein the first polynucleotide further comprises a first recognition site for a first nuclease agent; (b) introducing into the cell (i) a first nuclease agent, wherein the first nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site and the first insert polynucleotide further comprises (1) a first polynucleotide of interest; and, (2) a second polynucleotide encoding a second selection marker operably linked to a second promoter active in the cell, wherein the second polynucleotide comprises a second recognition site for a second nuclease agent, and the second polynucleotide comprising the second selection marker is flanked by a third target site and a fourth target site, the third target site corresponds to the third homology arm in the second targeting vector and the fourth target site corresponds to the fourth homology arm in the second targeting vector; (c) identifying at least one cell comprising the first insert polynucleotide integrated at the target locus; (d) introducing into the cell comprising the first insert polynucleotide integrated at the target locus, (i) a second nuclease agent, wherein the second nuclease agent induces a nick or double-strand break at the second recognition site; and, (ii) a second targeting vector comprising a second insert polynucleotide flanked by a third and a fourth homology arm wherein the second insert polynucleotide comprises (1) a second polynucleotide of interest; and, (2) a third polynucleotide encoding a third selection marker operably linked to a third promoter active in the cell, wherein the third polynucleotide comprises a third recognition site for a third nuclease agent; and, (b) identifying at least one cell comprising the second insert polynucleotide integrated at the target locus. In specific embodiments, the nick or double-strand break at the second recognition maker disrupts the activity of the second selection marker. In further embodiments, identifying at least one cell comprising in its genome the second insert polynucleotide integrated at the target locus comprises culturing the cell under conditions that identify cells which do not have the activity of the second selection marker. In further embodiments, identifying at least one cell comprising in its genome the second insert polynucleotide integrated at the target locus comprises identifying at least one cell comprising in its genome the second insert polynucleotide integrated at the third and the fourth target site.

The various methods set forth above can be sequentially repeated to allow for the targeted integration of any number of insert polynucleotides into a given targeted locus. Thus, the various methods provide for the insertion of at least 1, 2, 3, 4, 5, 6, 7, 8, 9, 10, 11, 12, 13, 14, 15, 16, 17, 18, 19, 20 or more insert polynucleotides into the target locus. In particular embodiments, such sequential tiling methods allow for the reconstruction of large genomic regions from a mammalian cell (i.e., a human, a non-human, a rodent, a mouse, a monkey, a rate a hamster, a domesticated mammal or an agricultural animal) into a targeted locus (i.e., a genomic locus). In such instances, the transfer and reconstruction of genomic regions that include both coding and non-coding regions allow for the complexity of a given region to be preserved by retaining, at least in part, the coding regions, the non-coding regions and the copy number variations found within the native genomic region. Thus, the various methods provide, for example, methods to generate "heterologous" or "exogenous" genomic regions within any mammalian cell or animal of interest. In one non-limiting example, a "humanized" genomic region within a non-human animal is generated.

When performing integration of multiple insert polynucleotides within a given target locus, the polynucleotides encoding the selection markers and comprising the nuclease agent recognition site can be alternated between integration rounds. For example, in specific methods, the first nuclease agent is different from the second nuclease agent and/or the first selection marker is different from the second selection marker. In other examples, when inserting three insert polynucleotides into a targeted locus, the first and the third selection markers can be identical to one another and, in specific embodiments, further comprise the same recognition site, and the second selection marker can be different from the first and third selection marker and contain a different recognition site. Selection of the selection markers and the recognition sites in such a manner minimizes the number or nuclease agents that must be generated, and thereby improves the efficiency and efficacy of the integration events.

C. Methods for Modifying One or More Target Loci Using a CRISPR/Cas System

Methods and compositions are provided for modifying one or more target loci of interest in a cell utilizing a CRISPR/Cas system as described elsewhere herein. For the CRISPR/Cas system, the terms "target site" or "target sequence" can be used interchangeably and include nucleic acid sequences present in a target DNA to which a DNA-targeting segment of a guide RNA (gRNA) will bind, provided sufficient conditions for binding exist. For example, the target site (or target sequence) within a target DNA is targeted by (or is bound by, or hybridizes with, or is complementary to) the Cas nuclease or gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA is referred to as the "complementary strand" and the strand of the target DNA that is complementary to the "complementary strand" (and is therefore not complementary to the Cas protein or gRNA) is referred to as the "noncomplementary strand" or "template strand."

The Cas protein may cleave the nucleic acid at a site within the target sequence or outside of the target sequence. The "cleavage site" includes the position of a nucleic acid wherein a Cas protein produces a single-strand break or a double-strand break. Sticky ends can also be produced by using two Cas9 protein which produce a single-strand break at cleavage sites on each strand. Site-specific cleavage of target DNA by Cas9 can occur at locations determined by both (i) base-pairing complementarity between the guide RNA and the target DNA; and (ii) a short motif, referred to as the protospacer adjacent motif (PAM), in the target DNA. For example, the cleavage site of Cas9 can be about 1 to about 10 or about 2 to about 5 base pairs (e.g., 3 base pairs) upstream of the PAM sequence. In some embodiments (e.g., when Cas9 from S. pyogenes, or a closely related Cas9, is used), the PAM sequence of the non-complementary strand can be 5'-XGG-3', where X is any DNA nucleotide and X is immediately 3' of the target sequence of the non-complementary strand of the target DNA. As such, the PAM sequence of the complementary strand would be 5'-CCY-3', where Y is any DNA nucleotide and Y is immediately 5' of the target sequence of the complementary strand of the target DNA. In some such embodiments, X and Y can be complementary and the X-Y base pair can be any basepair (e.g., X=C and Y=G; X=G and Y=C; X=A and Y=T, X=T and Y=A).

Thus, in some embodiments, the methods for modifying a target locus of interest in a cell comprise: (a) providing the cell comprising a first target locus comprising a nucleic acid encoding a first selection marker operably linked to a first promoter; (b) introducing into the cell (i) one or more expression constructs encoding a Cas protein and a first guide RNA (gRNA), each of which is operably linked to a promoter active in the cell, wherein the Cas protein induces a nick or a double-strand break at a first gRNA target site in the first nucleic acid, thereby disrupting expression or activity of the first selection marker, and (ii) a first targeting vector comprising a first insert nucleic acid comprising a second nucleic acid that encodes a second selection marker operably linked to a second promoter, wherein the first insert nucleic acid is flanked by a first and a second homology arm corresponding to a first and a second target site located in the first target locus; and (c) identifying a modified cell comprising the first insert nucleic acid at the first target locus, wherein the modified cell has the activity of the second selection marker but does not have the activity of the first selection marker, and wherein the first and the second selection markers are different. In one embodiment, the first gRNA does not hybridize to the first insert nucleic acid. In one embodiment, the target locus of interest is located in the genome of the cell. In another embodiment, the target locus of interest is located in a vector in the cell. In one embodiment, the identifying step (c) comprises culturing the cell under conditions that allow identification of the modified cell that has activity of the second selection marker but does not have the activity of the first selection marker.

In one embodiment, the method further comprises (d) introducing into the modified cell comprising the first insert nucleic acid at the first target locus (i) one or more nucleic acids encoding the Cas protein and a second gRNA, each of which is operably linked to the promoter active in the modified cell, wherein the Cas protein induces the nick or double-strand break at a second gRNA target site in the first insert nucleic acid comprising the second nucleic acid, thereby disrupting expression or activity of the second selection marker, and (ii) a second targeting vector comprising a second insert nucleic acid comprising a third nucleic acid encoding a third selection marker operably linked to a third promoter, wherein the second insert nucleic acid is flanked by third and fourth homology arms corresponding to a third and a fourth target site located in a second target locus; and (e) identifying a second modified cell comprising the second insert nucleic acid at the second target locus, wherein the second modified cell has the activity of the third selection marker but does not have the activity of the second selection marker, wherein the second and the third selection markers are different. In one embodiment, the first and the second target loci are located immediately adjacent to each other. In another embodiment, the first or the second target locus is located about 10 nucleotides to about 14 kb from the first or the second gRNA target site. In one embodiment, the second gRNA does not hybridize to the second insert nucleic acid. In one embodiment, the identifying step (e) comprises culturing the modified cell under conditions that allow identification of the second modified cell that has activity of the third selection marker but does not have the activity of the second selection marker.

In one embodiment, the method further comprises (f) introducing into the second modified cell comprising the second insert nucleic acid at the second target locus: (i) the one or more expression constructs encoding the Cas protein and a third gRNA, each of which operably linked to the promoter active in the second modified cell, wherein the Cas protein induces the nick or double-strand break at a third gRNA target site in the second insert nucleic acid comprising the third nucleic acid, thereby disrupting expression or activity of the third selection marker, and (ii) a third targeting vector comprising a third insert nucleic acid comprising a fourth nucleic acid that encodes a fourth selection marker operably linked to a fourth promoter, wherein the third insert nucleic acid is flanked by fifth and six homology arms corresponding to fifth and sixth target sites located in a third target locus; and (g) identifying a third modified cell comprising the third insert nucleic acid at the third target locus, wherein the third modified cell has the activity of the fourth selection marker but does not have the activity of the third selection marker, wherein the third and the fourth selection markers are different. In one embodiment, the second and third target loci are located immediately adjacent to each other. In another embodiment, the second or the third target locus is located about 10 nucleotides to about 14 kb from the first or the second gRNA target site.

In one embodiment, the first, the second, the third, or the fourth marker imparts resistance to an antibiotic. In one embodiment, the antibiotic comprises G418, hygromycin, blastocidin, neomycin, or puromycin. In one embodiment, the first, the second, the third, or the fourth selection markers comprise hypoxanthine-guanine phosphoribosyltransferase (HGPRT) or thymidine kinase of Herpes simplex virus (HSV-TK). In one embodiment, the first, the second, or the third gRNAs comprises (i) a nucleotide sequence that hybridizes to the first, the second or the third gRNA target site and (ii) a trans-activating CRISPR RNA (tracrRNA). In one embodiment, the first, the second, or the third target locus is located in close proximity to the first, the second or the third gRNA target site such that the nick or the double-strand break at the gRNA target site promotes homologous recombination of the targeting vector at the target locus. In one embodiment, the Cas protein is Cas9. In one embodiment, the first, the second, or the third gRNA target site is immediately flanked by a Protospacer Adjacent Motif (PAM) sequence.

In specific embodiments, the gRNA is designed to target a first antibiotic selection marker (e.g., Hyg$^r$) for the insertion of a first insert nucleic acid encoding a second selection marker (e.g., Neo$^r$), whereby insertion of the first insert nucleic acid disrupts the activity of the first antibiotic selection marker. A second gRNA expression plasmid can be designed to express gRNA that targets the second selection marker for insertion of a second insert nucleic acid encoding the first selection marker, whereby insertion of the second insert nucleic acid disrupts the activity of the second antibiotic selection marker. In this manner, gRNAs need only be designed that target each of two antibiotic selection makers that can be used in alternating nucleic acid inserts. Exemplary nucleic acids encoding gRNAs specific for Neo resistance selection markers can be found in SEQ ID NOs: 13, 14, 15, and 16. Exemplary nucleic acids encoding gRNAs specific for Hyg resistance selection markers can be found in SEQ ID NOs: 17, 18, 19, and 20.

In one embodiment, the cell is a prokaryotic cell. In another embodiment, the cell is a eukaryotic cell. In one embodiment, the eukaryotic cell is a mammalian cell or a non-human mammalian cell. In one embodiment, the mammalian cell is a fibroblast cell. In one embodiment, the mammalian cell is a human fibroblast cell. In one embodiment, the mammalian cell is a human adult stem cell. In one embodiment, the mammalian cell is a developmentally restricted progenitor cell. In one embodiment, the mammalian cell is a developmentally restricted human progenitor cell.

In one embodiment, the mammalian cell is a non-human mammalian cell. In one embodiment, the mammalian cell is from a rodent. In one embodiment, the rodent is a rat, a mouse, or a hamster. In one embodiment, the eukaryotic cell is a pluripotent cell. In one embodiment, the pluripotent cell is a hematopoietic stem cell or a neuronal stem cell. In one embodiment, the pluripotent cell is a human induced pluripotent stem (iPS) cell. In one embodiment, the pluripotent cell is a non-human ES cell, a human ES cell, a rodent embryonic stem (ES) cell, a mouse embryonic stem (ES) cell or a rat embryonic stem (ES) cell.

In one embodiment, the first, the second, or the third gRNA target site is located in an intron, an exon, a promoter, or a promoter regulatory region in the first, the second, or the third nucleic acid that encodes the first, the second, or the third selection marker. In one embodiment, the first, second, or third targeting vector is at least about 10 kb. In one embodiment, the first, the second, or the third insert nucleic acid ranges from about 5 kb to about 300 kb.

In one embodiment, the first, second, or third insert nucleic acid comprises a genomic region of the human T cell receptor alpha locus. In one embodiment, the genomic region comprises at least one variable region gene segment and/or a joining region gene segment of the human T cell receptor alpha locus.

In one embodiment, the first and the third selection markers are the same. In one embodiment, the first and the third selection markers are the same and the second and the fourth selection markers are the same. In one embodiment, the first and the third gRNAs are the same.

In some embodiments, the methods for modifying a target locus of interest in a cell comprise: (a) providing the cell comprising a first target locus comprising a nucleic acid encoding a first selection marker operably linked to a first promoter; (b) introducing into the cell (i) one or more expression constructs encoding a Cas protein and a first gRNA, each of which is operably linked to a promoter active in the cell, wherein the Cas protein induces a nick or a double-strand break at a first gRNA target site in the first nucleic acid, thereby disrupting expression or activity of the first selection marker, and (ii) a first targeting vector comprising a first insert nucleic acid comprising a second nucleic acid that encodes a second selection marker operably linked to a second promoter, wherein the first insert nucleic acid is flanked by a first and a second homology arm corresponding to a first and a second target site located in the first target locus; (c) identifying a modified cell comprising the first insert nucleic acid at the first target locus, wherein the modified cell has the activity of the second selection marker but does not have the activity of the first selection marker, and wherein the first and the second selection markers are different; (d) introducing into the modified cell comprising the first insert nucleic acid at the first target locus: (i) one or more nucleic acids encoding the Cas protein and a second gRNA, each of which operably linked to the promoter active in the modified cell, wherein the Cas protein induces the nick or double-strand break at a second gRNA target site in the first insert nucleic acid comprising the second nucleic acid, thereby disrupting expression or activity of the second selection marker; and (ii) a second targeting vector comprising a second insert nucleic acid comprising a third nucleic acid encoding a third selection marker operably linked to a third promoter, wherein the second insert nucleic acid is flanked by third and fourth homology arms corresponding to a third and a fourth target site located in a second target locus; and (e) identifying a second modified cell comprising the second insert nucleic acid at the second target locus, wherein the second modified cell has the activity of the third selection marker but does not have the activity of the second selection marker, wherein the first and third selection markers are the same, and the second and the third selection markers are different.

In other embodiments, the methods for modifying a target locus of interest in a cell comprise: (a) providing the cell comprising a first target locus comprising a nucleic acid encoding a first selection marker operably linked to a first promoter; (b) introducing into the cell (i) one or more expression constructs encoding a Cas protein and a first gRNA, each of which is operably linked to a promoter active in the cell, wherein the Cas protein induces a nick or a double-strand break at a first gRNA target site in the first nucleic acid, thereby disrupting expression or activity of the first selection marker, and (ii) a first targeting vector comprising a first insert nucleic acid comprising a second nucleic acid that encodes a second selection marker operably linked to a second promoter, wherein the first insert nucleic acid is flanked by a first and a second homology arm corresponding to a first and a second target site located in the first target locus; (c) identifying a modified cell comprising the first insert nucleic acid at the first target locus, wherein the modified cell has the activity of the second selection marker but does not have the activity of the first selection marker, and wherein the first and the second selection markers are different; (d) introducing into the modified cell comprising the first insert nucleic acid at the first target locus: (i) one or more nucleic acids encoding the Cas protein and a second gRNA, each of which operably linked to the promoter active in the modified cell, wherein the Cas protein induces the nick or double-strand break at a second gRNA target site in the first insert nucleic acid comprising the second nucleic acid, thereby disrupting expression or activity of the second selection marker; and (ii) a second targeting vector comprising a second insert nucleic acid comprising a third nucleic acid encoding a third selection marker operably linked to a third promoter, wherein the second insert nucleic acid is flanked by third and fourth homology arms corresponding to a third and a fourth target site located in a second target locus; (e) identifying a second modified cell comprising the second insert nucleic acid at the second target locus, wherein the second modified cell has the activity of the third selection marker but does not have the activity of the second selection marker, wherein the second and the third selection markers are different; (f) introducing into the second modified cell comprising the second insert nucleic acid at the second target locus: (i) the one or more expression constructs encoding the Cas protein and a third gRNA, each of which operably linked to the promoter active in the second modified cell, wherein the Cas protein induces the nick or double-strand break at a third gRNA target site in the second insert nucleic acid comprising the third nucleic acid, thereby disrupting expression or activity of the third selection marker; and (ii) a third targeting vector comprising a third insert nucleic acid comprising a fourth nucleic acid that encodes a fourth selection marker operably linked to a fourth promoter, wherein the third insert nucleic acid is flanked by fifth and six homology arms corresponding to fifth and sixth target sites located in a third target locus; and (g) identifying a third modified cell comprising the third insert nucleic acid at the third target locus, wherein the third modified cell has the activity of the fourth selection marker but does not have the activity of the third selection marker, wherein the third and the fourth selection markers are different. In some embodiments, the first and the third selection markers are the same and the second and the fourth selection markers are the same. In one embodiment, the first and the third selection markers are the same, the second and the fourth selection markers are the same, and the first and the third gRNAs are the same.

IV. Polynucleotides of Interest

Any polynucleotide of interest may be contained in the various insert polynucleotides and thereby integrated at the target locus. The methods disclosed herein, provide for at least 1, 2, 3, 4, 5, 6 or more polynucleotides of interest to be integrated into the targeted locus.

The polynucleotide of interest within the insert polynucleotide when integrated at the target locus can introduce one or more genetic modifications into the cell. The genetic modification can comprise a deletion of an endogenous nucleic acid sequence and/or the addition of an exogenous or heterologous or ortholgous polynucleotide into the target locus. In one embodiment, the genetic modification comprises a replacement of an endogenous nucleic acid sequence with an exogenous polynucleotide of interest at the target locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof. Such modifications may occur upon integration of the first, second, third, fourth, fifth, six, seventh, or any subsequent insert polynucleotides into the target locus.

The polynucleotide of interest within the insert polynucleotide and/or integrated at the target locus can comprise a sequence that is native or homologous to the cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. The term "homologous" in reference to a sequence includes a sequence that is native to the cell. The term "heterologous" in reference to a sequence includes a sequence that originates from a foreign species, or, if from the same species, is substantially modified from its native form in composition and/or locus by deliberate human intervention. The term "exogenous" in reference to a sequence includes a sequence that originates from a foreign species. The term "orthologous" includes a polynucleotide from one species that is functionally equivalent to a known reference sequence in another species (i.e., a species variant). The polynucleotide of interest can be from any organism of interest including, but not limited to, non-human, a rodent, a hamster, a mouse, a rat, a human, a monkey, an agricultural mammal or a non-agricultural mammal. The polynucleotide of interest can further comprise a coding region, a non-coding region, a regulatory region, or a genomic DNA. Thus, the 1st, 2nd, 3rd, 4th, 5th, 6th, 7th, and/or any of the subsequent insert polynucleotides can comprise such sequences.

In one embodiment, the polynucleotide of interest within the insert polynucleotide and/or integrated at the target locus is homologous to a mouse nucleic acid sequence, a human nucleic acid, a non-human nucleic acid, a rodent nucleic acid, a rat nucleic acid, a hamster nucleic acid, a monkey nucleic acid, an agricultural mammal nucleic acid, or a non-agricultural mammal nucleic acid. In still further embodiments, the polynucleotide of interest integrated at the target locus is a fragment of a genomic nucleic acid. In one embodiment, the genomic nucleic acid is a mouse genomic nucleic acid, a human genomic nucleic acid, a non-human nucleic acid, a rodent nucleic acid, a rat nucleic acid, a hamster nucleic acid, a monkey nucleic acid, an agricultural mammal nucleic acid or a non-agricultural mammal nucleic acid or a combination thereof.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

The polynucleotide of interest within the insert polynucleotide and/or inserted at the target locus can encode a polypeptide, can encode an miRNA, or it can comprise any regulatory regions or non-coding regions of interest including, for example, a regulatory sequence, a promoter sequence, an enhancer sequence, a transcriptional repressor-binding sequence, or a deletion of a non-protein-coding sequence. In addition, the polynucleotide of interest within the insert polynucleotide and/or inserted at the target locus can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the polynucleotide of interest within the insert polynucleotide and/or inserted at the target locus encodes a protein expressed in a bone marrow or a bone marrow-derived cell. In one embodiment, the polynucleotide of interest within the insert polynucleotide and/or integrated at the target locus encodes a protein expressed in a spleen cell. In still further embodiments, the polynucleotide of interest within the insert polynucleotide and/or inserted at the target locus encodes a protein expressed in a B cell, encodes a protein expressed in an immature B cell or encodes a protein expressed in a mature B cell.

In one embodiment, the polynucleotide of interest within the insert polynucleotide and/or inserted at the target locus comprises a genomic nucleic acid sequence that encodes an immunoglobulin heavy chain variable region amino acid sequence. The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four framework (FR) regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an epitope (e.g., recognizing the epitope with a KD in the micromolar, nanomolar, or picomolar range), that is capable of expressing and secreting from a cell, and that comprises at least one CDR. Heavy chain variable domains are encoded by variable region nucleotide sequence, which generally comprises VH, DH, and JH segments derived from a repertoire of VH, DH, and JH segments present in the germline. Sequences, locations and nomenclature for V, D, and J heavy chain segments for various organisms can be found in IMGT database, which is accessible via the internet on the world wide web (www) at the URL "imgt.org."

In one embodiment, the polynucleotide of interest within the insert polynucleotide and/or integrated at the target locus comprises a genomic nucleic acid sequence that encodes a human immunoglobulin heavy chain variable region amino acid sequence. In one embodiment, the genomic nucleic acid sequence comprises an unrearranged human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a mouse immunoglobulin heavy chain constant region nucleic acid sequence or human immunoglobulin heavy chain constant region nucleic acid sequence, or a combination thereof. In one embodiment, the immunoglobulin heavy chain constant region nucleic acid sequence is selected from a CH1, a hinge, a CH2, a CH3, and a combination thereof. In one embodiment, the heavy chain constant region nucleic acid sequence comprises a CH1-hinge-CH2-CH3. In one embodiment, the genomic nucleic acid sequence comprises a rearranged human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a mouse immunoglobulin heavy chain constant region nucleic acid sequence or a human immunoglobulin heavy chain constant region nucleic acid sequence, or a combination thereof. In one embodiment, the immunoglobulin heavy chain constant region nucleic acid sequence is selected from a CH1, a hinge, a CH2, a CH3, and a combination thereof. In one embodiment, the heavy chain constant region nucleic acid sequence comprises a CH1-hinge-CH2-CH3.

In one embodiment, the polynucleotide of interest within the insert polynucleotide and/or integrated at the target locus comprises a genomic nucleic acid sequence that encodes an immunoglobulin light chain variable region amino acid sequence. The phrase "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four FRs, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain VL and light chain JL gene segments, derived from a repertoire of light chain V and J gene segments present in the germline. Sequences, locations and nomenclature for light chain V and J gene segments for various organisms can be found in IMGT database, which is accessible via the internet on the world wide web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

In one embodiment, the polynucleotide of interest within the insert polynucleotide and/or integrated at the target locus comprises a genomic nucleic acid sequence that encodes a human immunoglobulin light chain variable region amino acid sequence. In one embodiment, the genomic nucleic acid sequence comprises an unrearranged human λ and/or κ light chain variable region nucleic acid sequence. In one embodiment, the genomic nucleic acid sequence comprises a rearranged human λ and/or κ light chain variable region nucleic acid sequence. In one embodiment, the unrearranged or rearranged λ and/or κ light chain variable region nucleic acid sequence is operably linked to a mouse, rat, or human immunoglobulin light chain constant region nucleic acid sequence selected from a λ light chain constant region nucleic acid sequence and a κ light chain constant region nucleic acid sequence.

The polynucleotide of interest within the insert polynucleotide and/or integrated at the target locus can encode an extracellular protein or a ligand for a receptor. In specific embodiments, the encoded ligand is a cytokine. Cytokines of interest includes a chemokine selected from CCL, CXCL, CX3CL, and XCL. The cytokine can also comprise a tumor necrosis factor (TNF). In still other embodiments, the cytokine is an interleukin (IL). In one embodiment, the interleukin is selected from IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36. In one embodiment, the interleukin is IL-2. In specific embodiments, such polynucleotides of interest within the insert polynucleotide and/or integrated at the target locus are from a human and, in more specific embodiments, can comprise human sequence.

The polynucleotide of interest within the insert polynucleotide and/or integrated at the target locus can encode a cytoplasmic protein or a membrane protein. In one embodiment, the membrane protein is a receptor, such as, a cytokine receptor, an interleukin receptor, an interleukin 2 receptor alpha, an interleukin 2 receptor beta, or an interleukin 2 receptor gamma.

The polynucleotide of interest within the insert polynucleotide and/or integrated at the target locus can comprise a polynucleotide encoding at least a region of a T cell receptor, including the T cell receptor alpha. In specific methods each of the insert polynucleotides comprise a region of the T cell receptor locus (i.e. the T cell receptor alpha locus) such that upon completion of the serial integration, a portion or the entirety of the T cell receptor locus has been integrated at the target locus. Such insert polynucleotides can comprise at least one or more of a variable segment or a joining segment of a T cell receptor locus (i.e. of the T cell receptor alpha locus). In still further the polynucleotide of interest encoding the region of the T cell receptor can be from, for example, a mammal, a non-human mammal, rodent, mouse, rat, a human, a monkey, an agricultural mammal or a domestic mammal polynucleotide encoding a mutant protein.

In other embodiments, the polynucleotide of interest integrated at the target locus encodes a nuclear protein. In one embodiment, the nuclear protein is a nuclear receptor. In specific embodiments, such polynucleotides of interest within the insert polynucleotide and/or integrated at the target locus are from a human and, in more specific embodiments, can comprise human genomic sequence.

The polynucleotide of interest within the insert polynucleotide and/or integrated at the target genomic locus can comprises a genetic modification in a coding sequence. Such genetic modifications include, but are not limited to, a deletion mutation of a coding sequence or the fusion of two coding sequences.

The polynucleotide of interest within the insert polynucleotide and/or integrated at the target locus can comprise a polynucleotide encoding a mutant protein. In one embodiment, the mutant protein is characterized by an altered binding characteristic, altered localization, altered expression, and/or altered expression pattern. In one embodiment, the polynucleotide of interest within the insert polynucleotide and/or integrated at the target locus comprises at least one disease allele, including for example, an allele of a neurological disease, an allele of a cardiovascular disease, an allele of a kidney disease, an allele of a muscle disease, an allele of a blood disease, an allele of a cancer-causing gene, or an allele of an immune system disease. In such instances, the disease allele can be a dominant allele or the disease allele is a recessive allele. Moreover, the disease allele can comprise a single nucleotide polymorphism (SNP) allele. The polynucleotide of interest encoding the mutant protein can be from any organism, including, but not limited to, a mammal, a non-human mammal, rodent, mouse, rat, a human, a monkey, an agricultural mammal or a domestic mammal polynucleotide encoding a mutant protein.

The polynucleotide of interest within the insert polynucleotide and/or integrated at the target locus can also comprise a regulatory sequence, including for example, a promoter sequence, an enhancer sequence, or a transcriptional repressor-binding sequence. In specific embodiments, the polynucleotide of interest within the insert polynucleotide and/or integrated at the target locus comprises a polynucleotide having a deletion of a non-protein-coding sequence, but does not comprise a deletion of a protein-coding sequence. In one embodiment, the deletion of the non-protein-coding sequence comprises a deletion of a regulatory sequence. In another embodiment, the deletion of the regulatory element comprises a deletion of a promoter sequence. In one embodiment, the deletion of the regulatory element comprises a deletion of an enhancer sequence. Such a polynucleotide of interest can be from any organism, including, but not limited to, a mammal, a non-human mammal, rodent, mouse, rat, a human, a monkey, an agricultural mammal or a domestic mammal polynucleotide encoding a mutant protein.

V. Methods of Introducing Sequences and Generation of Transgenic Animals

As outlined above, methods and compositions are provided herein to allow for the targeted integration of one or more polynucleotides of interest. Such systems employ a variety of components and for ease of reference, herein the term "targeted integration system" generically refers to all the components required for an integration event (i.e. the various nuclease agents, recognition sites, insert DNA polynucleotides, targeting vectors, target locus, and polynucleotides of interest).

The methods provided herein comprise introducing into a cell one or more polynucleotides or polypeptide constructs comprising the various components of the targeted integration system. The term "introducing" includes presenting to the cell the sequence (polypeptide or polynucleotide) in such a manner that the sequence gains access to the interior of the cell. The methods provided herein do not depend on a particular method for introducing any component of the targeted integration system into the cell, only that the polynucleotide gains access to the interior of a least one cell. Methods for introducing polynucleotides into various cell types are known in the art and include, but are not limited to, stable transfection methods, transient transfection methods, and virus-mediated methods.

In some embodiments, the cells employed in the methods and compositions have a DNA construct stably incorporated into their genome. "Stably incorporated" or "stably introduced" means the introduction of a polynucleotide into the cell such that the nucleotide sequence integrates into the genome of the cell and is capable of being inherited by progeny thereof. Any protocol may be used for the stable incorporation of the DNA constructs or the various components of the targeted integration system.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). Virology 52 (2): 456-67, Bacchetti et al. (1977) Proc Natl Acad Sci USA 74 (4): 1590-4 and, Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation; Sono-poration; and optical transfection. Particle-based transfection include the use of a gene gun, magnet assisted transfection (Bertram, J. (2006) Current Pharmaceutical Biotechnology 7, 277-28). Viral methods can also be used for transfection.

In one embodiment, the nuclease agent is introduced into the cell simultaneously with the targeting vector or the large targeting vector (LTVEC). Alternatively, the nuclease agent is introduced separately from the targeting vector or the LTVEC over a period of time. In one embodiment, the nuclease agent is introduced prior to the introduction of the targeting vector or the LTVEC, while in other embodiments, the nuclease agent is introduced following introduction of the targeting vector or the LTVEC.

Non-human mammalian animals can be generated employing the various methods disclosed herein. Such methods comprises (1) integrating one or more polynucleotide of interest at the target locus of a pluripotent cell of the non-human animal to generate a genetically modified pluripotent cell comprising the insert polynucleotide in the targeted locus employing the methods disclosed herein; (2) selecting the genetically modified pluripotent cell having the one or more polynucleotides of interest at the target locus; (3) introducing the genetically modified pluripotent cell into a host embryo of the non-human animal at a pre-morula stage; and (4) implanting the host embryo comprising the genetically modified pluripotent cell into a surrogate mother to generate an F0 generation derived from the genetically modified pluripotent cell. The non-human animal can be a non-human mammal, a rodent (e.g., a mouse, a rat, a hamster), a monkey, an agricultural mammal or a domestic mammal. The pluripotent cell can be a human ES cell, a human iPS cell, a non-human ES cell, a rodent ES cell (e.g., a mouse ES cell, a rat ES cell, or a hamster ES cell), a monkey ES cell, an agricultural mammal ES cell or a domesticated mammal ES cell. See, e.g., U.S. Publication No. 2014/0235933; U.S. Publication No. 2014/0310828; and Tong et al. (2010) *Nature,* 467(7312):211-213, each of which is herein incorporated by reference in its entirety.

Nuclear transfer techniques can also be used to generate the non-human mammalian animals. Briefly, methods for nuclear transfer include the steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

Other methods for making a non-human animal comprising in its germline one or more genetic modifications as described herein is provided, comprising: (a) modifying a targeted locus of a non-human animal in a prokaryotic cell employing the various methods described herein; (b) selecting a modified prokaryotic cell comprising the genetic modification at the targeted locus; (c) isolating the genetically modified targeting vector from the modified prokaryotic cell; (d) introducing the genetically modified targeting vector into a pluripotent cell of the non-human animal to generate a genetically modified pluripotent cell comprising the insert nucleic acid at the targeted locus; (e) selecting the genetically modified pluripotent cell; (f) introducing the genetically modified pluripotent cell into a host embryo of the non-human animal at a pre-morula stage; and (g) implanting the host embryo comprising the genetically modified pluripotent cell into a surrogate mother to generate an F0 generation derived from the genetically modified pluripotent cell. In such methods the targeting vector can comprise a large targeting vector. The non-human animal can be a non-human mammal, a rodent, a mouse, a rat, a hamster, a monkey, an agricultural mammal or a domestic mammal. The pluripotent cell can be a human ES cell, a human iPS cell, a non-human ES cell, a rodent ES cell (e.g., a mouse ES cell, a rat ES cell, or a hamster ES cell), a monkey ES cell, an agricultural mammal ES cell or a domestic mammal ES cell.

In further methods, the isolating step (c) further comprises (c1) linearizing the genetically modified targeting vector (i.e., the genetically modified LTVEC). In still further embodiments, the introducing step (d) further comprises (d1) introducing a nuclease agent as described herein into the pluripotent cell. In other embodiments, the introducing step (d) further comprises (d2) wherein the pluripotent cell of the of the non-human mammal comprises a target locus comprising a first polynucleotide encoding a first selection marker operably linked to a first promoter active in the cell, wherein the first polynucleotide further comprises a first recognition site for a first nuclease agent, and introducing a nuclease agent into the pluripotent cell, wherein the first nuclease agent induces a nick or double-strand break at the first recognition site. Further introducing into the pluripotent cell is a first targeting vector comprising the genetically modified targeting vector from the genome of the modified prokaryotic cell. The modified targeting vector comprises a first and a second homology arm that correspond to a first and a second target site in sufficient proximity to the first recognition site within the genome of the pluripotent cell of the non-human mammal. In one embodiment, selecting steps (b) and/or (e) are carried out by applying a selection agent as described herein to the prokaryotic cell or the pluripotent cell. In one embodiment, selecting steps (b) and/or (e) are carried out via a modification of allele (MOA) assay as described herein.

Further methods for modifying a target locus of a mammalian cell via bacterial homologous recombination (BHR) in a prokaryotic cell are provided and comprise: (a) providing a prokaryotic cell comprising a target locus comprising a first polynucleotide encoding a first selection marker operably linked to a first promoter active in the prokaryotic cell, wherein the first polynucleotide further comprises a first recognition site for a first nuclease agent, (b) introducing into the prokaryotic cell a targeting vector comprising an insert polynucleotide flanked with a first upstream homology arm and a first downstream homology arm, wherein the insert polynucleotide comprises a mammalian region, and introducing into the prokaryotic cell a nuclease agent that makes a nick or double-strand break at or near the first recognition site, and (c) selecting a targeted prokaryotic cell comprising the insert polynucleotide at the target locus, wherein the prokaryotic cell is capable of expressing recombinogenic proteins and enzymes that mediate the BHR. Steps (a)-(c) can be serially repeated as disclosed herein to allow the introduction of multiple insert polynucleotides at the targeted locus in the prokaryotic cell. Once the targeted locus is "built" with the prokaryotic cell, a targeting vector comprising the modified target locus can be isolated from the prokaryotic cell and introduced into a target locus within a non-human mammalian cell. Mammalian cells comprising the modified locus can then be made into non-human transgenic animals.

In some embodiments, various genetic modifications of the target loci described herein can be carried out by a series of homologous recombination reactions (BHR) in bacterial cells using Bacterial Artificial Chromosome (BAC) DNA using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, Nature Biotechnology 21(6): 652-659, which is incorporated herein by reference in their entireties).

In some embodiments, targeted mammalian ES cells (i.e., from non-human mammals, rodents (e.g., mice, rats, or hamsters), agricultural mammals, domestic mammals, monkeys, etc.) comprising various genetic modifications as described herein are introduced into a pre-morula stage embryo from a corresponding organism, e.g., an 8-cell stage mouse embryo, via the VELOCIMOUSE® method (see, e.g., U.S. Pat. No. 7,576,259, 7,659,442, 7,294,754, and US 2008-0078000 A1, all of which are incorporated by reference herein in their entireties). The non-human mammalian embryo comprising the genetically modified ES cells is incubated until the blastocyst stage and then implanted into a surrogate mother to produce an F0. In some other embodiments, targeted mammalian ES cells comprising various genetic modifications as described herein are introduced into a blastocyst stage embryo. Non-human mammals bearing the genetically modified locus can be identified via modification of allele (MOA) assay as described herein. The resulting F0 generation non-human mammal derived from the genetically modified ES cells is crossed to a wild-type non-human mammal to obtain F1 generation offspring. Following genotyping with specific primers and/or probes, F1 non-human mammals that are heterozygous for the genetically modified locus are crossed to each other to produce non-human mammals that are homozygous for the genetically modified locus.

VI. Cells

The various methods described herein employ a locus targeting system in a cell. Such cells include prokaryotic cells such as bacterial cells including *E. coli*, or eukaryotic cells such as yeast, insect, amphibian, bird (e.g., chicken cells), plant, or mammalian cells, including, but not limited to a mouse cell, a rat cell, a rabbit cell, a pig cell, a bovine cell, a deer cell, a sheep cell, a goat cell, a cat cell, a dog cell, a ferret cell, a primate (e.g., marmoset, rhesus monkey) cell, and the like and cells from domesticated mammals or cells from agricultural mammals. Some cells are non-human, particularly non-human mammalian cells. In some embodiments, for those mammals for which suitable genetically modifiable pluripotent cells are not readily available, other methods are employed to reprogram somatic cells into pluripotent cells, e.g., via introduction into somatic cells of a combination of pluripotency-inducing factors, including, but not limited to, Oct3/4, Sox2, KLF4, Myc, Nanog, LIN28, and Glis1.

In one embodiment, the eukaryotic cell is a pluripotent cell. In one embodiment, the pluripotent cell is an embryonic stem (ES) cell. The term "embryonic stem cell" or "ES cell" includes an embryo-derived totipotent or pluripotent cell that is capable of undifferentiated proliferation in vitro, and is capable of contributing to any tissue of the developing embryo upon introduction into an embryo. The term "pluripotent cell" includes an undifferentiated cell that possesses the ability to develop into more than one differentiated cell type. The term "germline" in reference to a polynucleotide sequence includes a nucleic acid sequence that can be passed to progeny.

The pluripotent cell can be a non-human ES cell or an induced pluripotent stem (iPS) cell. In one embodiment, the induced pluripotent (iPS) cell is derived from a fibroblast. In specific embodiments, the induced pluripotent (iPS) cell is derived from a human fibroblast. In some embodiments, the pluripotent cell is a hematopoietic stem cell (HSC), a neuronal stem cell (NSC), or an epiblast stem cell. The pluripotent cell can also be a developmentally restricted progenitor cell. In further embodiments, the pluripotent cell is a rodent pluripotent cell. In one embodiment, the rodent pluripotent cell is a rat pluripotent cell or a rat ES cell. In other embodiments, the rodent pluripotent cell is a mouse pluripotent cell or a mouse ES cell.

In other embodiments, the mammalian cell can be immortalized mouse cell, rat cell or human cell. In one embodiment, the mammalian cell is a human fibroblast, while in other embodiments, the mammalian cell is a cancer cell, including a human cancer cell.

In still further embodiments, the mammal is a human and the targeting is carried out using an ex vivo human cell.

In one embodiment, the mammalian cell is a human cell isolated from a patient having a disease and/or comprises a human polynucleotide encoding a mutant protein. In one embodiment, the mutant human protein is characterized by an altered binding characteristic, altered localization, altered expression, and/or altered expression pattern. In one embodiment, the human nucleic acid sequence comprises at least one human disease allele. In one embodiment, the human nucleic acid sequence comprises at least one human disease allele. In one embodiment, the human disease allele is an allele of a neurological disease. In one embodiment, the human disease allele is an allele of a cardiovascular disease. In one embodiment, the human disease allele is an allele of a kidney disease. In one embodiment, the human disease allele is an allele of a muscle disease. In one embodiment, the human disease allele is an allele of a blood disease. In one embodiment, the human disease allele is an allele of a cancer-causing gene. In one embodiment, the human disease allele is an allele of an immune system disease. In one embodiment, the human disease allele is a dominant allele. In one embodiment, the human disease allele is a recessive allele. In one embodiment, the human disease allele comprises a single nucleotide polymorphism (SNP) allele.

When the cell comprises a prokaryotic cell, in specific embodiments, the prokaryotic cell is a recombination-competent strain of *E. coli*. In one embodiment, the prokaryotic cell comprises a nucleic acid that encodes recombinogenic proteins and enzymes. In one embodiment, the prokaryotic cell does not comprise the nucleic acid that encodes the recombinogenic proteins and enzymes, and the nucleic acid encoding the recombinogenic proteins and enzymes is introduced into the prokaryotic cell. In one embodiment, the nucleic acid comprises a DNA or an mRNA encoding the recombinogenic proteins and enzymes. In one embodiment the nucleic acid encoding the recombinogenic proteins and enzymes is pABG. In one embodiment, the recombinogenic proteins and enzymes are expressed under the control of an inducible promoter. In one embodiment, expression of the recombinogenic proteins and enzymes is controlled by arabinose.

VII. Expression Cassettes

Provided herein are polynucleotides or nucleic acid molecules comprising the various components of the targeted integration system provided herein (i.e. nuclease agents, recognition sites, insert polynucleotides, polynucleotides of interest, targeting vectors, selection markers and other components).

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Polynucleotides can comprise deoxyribonucleotides and ribonucleotides include both naturally occurring molecules and synthetic analogues, and any combination these. The polynucleotides provided herein also encompass all forms of sequences including, but not limited to, single-stranded forms, double-stranded forms, hairpins, stem-and-loop structures, and the like.

Further provided are recombinant polynucleotides comprising the various components of the targeted integration system. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Genetic elements required to successfully transform, select, and propagate host cells and comprising any of the isolated nucleic acid fragments are provided herein. Screening may be accomplished by Southern analysis of DNA, Northern analysis of mRNA expression, immunoblotting analysis of protein expression, or phenotypic analysis, among others.

In specific embodiments, one or more of the components of the targeted integration system described herein can be provided in an expression cassette for expression in a prokaryotic cell, a eukaryotic cell, a bacterial, a yeast cell, or a mammalian cell or other organism or cell type of interest.

The cassette can include 5' and 3' regulatory sequences operably linked to a polynucleotide provided herein. "Operably linked" includes a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The cassette may additionally contain at least one additional polynucleotide of interest to be co-introduced into the organism. Alternatively, the additional polynucleotide of interest can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

The expression cassette containing the polynucleotides provided herein can also comprise a selection marker gene for the selection of transformed cells. Selection marker genes are utilized for the selection of transformed cells or tissues.

Where appropriate, the sequences employed in the methods and compositions (i.e., the polynucleotide of interest, the nuclease agent, etc.) may be optimized for increased expression in the cell. That is, the genes can be synthesized using codons preferred in a given cell of interest including, for example, mammalian-preferred codons, human-preferred codons, rodent-preferred codon, mouse-preferred codons, rat-preferred codons, etc. for improved expression.

VIII. Sequence Identity

The methods and compositions provided herein employ a variety of different components of the targeted integration system (i.e. nuclease agents, recognition sites, insert polynucleotides, polynucleotides of interest, targeting vectors, selection markers and other components). It is recognized throughout the description that some components of the targeted integration system can have active variants and fragments. Such components include, for example, nuclease agents (i.e. engineered nuclease agents), nuclease agent recognition sites, polynucleotides of interest, target sites and corresponding homology arms of the targeting vector. Biological activity for each of these components is described elsewhere herein.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" means any sequence comparison program that, for any two sequences in question, generates an alignment having identical nucleotide or amino acid residue matches and an identical percent sequence identity when compared to the corresponding alignment generated by GAP Version 10.

Non-limiting embodiments include:

1. A method for modifying a target locus in a cell comprising: (a) providing a cell comprising a target locus that comprises a first polynucleotide encoding a first selection marker operably linked to a first promoter active in the cell, wherein the first polynucleotide further comprises a first recognition site for a first nuclease agent, (b) introducing into the cell (i) a first nuclease agent, wherein the first nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site; and, (c) identifying at least one cell comprising the first insert polynucleotide integrated at the target locus.

2. A method for modifying a target locus in a cell, comprising: (a) providing a cell comprising a first target locus comprising a first polynucleotide encoding a first selection marker operably linked to a first promoter, wherein the first polynucleotide further comprises a first recognition site for a first nuclease agent, (b) introducing into the cell: (i) one or more expression constructs encoding a first nuclease agent which is operably linked to a promoter active in the cell, wherein the first nuclease agent induces a nick or a double-strand break at a first recognition site in the first polynucleotide, thereby disrupting expression or activity of the first selection marker; and (ii) a first targeting vector comprising a first insert polynucleotide comprising a second polynucleotide that encodes a second selection marker operably linked to a second promoter, wherein the first insert nucleic acid is flanked by a first and a second homology arm corresponding to a first and a second target site located in the first target locus; and (c) identifying a modified cell comprising the first insert nucleic acid at the first target locus, wherein the modified cell has the activity of the second selection marker but does not have the activity of the first selection marker, and wherein the first and the second selection markers are different.

3. The method of embodiment 1 or 2, wherein the target locus is in the genome of the cell.

4. The method of embodiment 1 or 2, wherein the target locus located in a vector in the cell.

5. The method of any one of embodiments 1-4, wherein the nick or double strand break at the first recognition site disrupts the activity of the first selection marker.

6. The method of embodiment 1, 2, 3, 4, or 5, wherein the identifying step (c) comprises culturing the cells under conditions that allow identification of cells that do not have an activity of the first selection marker.

7. The method of any one of embodiments 1-6, wherein the first polynucleotide comprising the first selection marker is flanked by a first target site and a second target site.

8. The method of embodiment 7, wherein the identifying step (c) comprises identifying at least one cell comprising the first insert polynucleotide integrated at the first and the second target site.

9. The method of any one of embodiments 1-8, wherein the first insert polynucleotide comprises: (a) a first polynucleotide of interest; and, (b) a second polynucleotide encoding a second selection marker operably linked to a second promoter active in the cell, wherein the second polynucleotide comprises a second recognition site for a second nuclease agent.

10. The method of embodiment 9, wherein the method further comprises (a) introducing into the cell comprising the first insert polynucleotide integrated at the target locus, (i) a second nuclease agent, wherein the second nuclease agent induces a nick or double-strand break at the second recognition site; and, (ii) a second targeting vector comprising a second insert polynucleotide flanked by a third and a fourth homology arm corresponding to a third and a fourth target site located in sufficient proximity to the second recognition site; and, (b) identifying at least one cell comprising the second insert polynucleotide integrated at the target locus.

11. The method of embodiment 10, wherein the nick or double-strand break at the second recognition site disrupts the activity of the second selection marker.

12. The method of embodiment 11, wherein the identifying step (b) comprises culturing the cell under conditions that allow identification of cells that do not have the activity of the second selection marker.

13. The method of embodiment 10, 11, or 12, wherein the second polynucleotide comprising the second selection marker is flanked by the third target site and the fourth target site.

14. The method of embodiment 13, wherein the identifying step (b) comprises identifying at least one cell comprising the second insert polynucleotide integrated at the third and the fourth target site.

15. The method of any one of embodiments 10-14, wherein the second insert polynucleotide comprises: (a) a second polynucleotide of interest; and, (b) a third polynucleotide encoding a third selection marker operably linked to a third promoter active in the cell, wherein the third polynucleotide comprises a third recognition site for a third nuclease agent.

16. The method of any one of embodiments 9-15, wherein the first nuclease agent is different from the second nuclease agent.

17. The method of any one of embodiments 9-16, wherein the first selection marker is different from the second selection marker.

18. The method of embodiment 15, wherein the first and the third nuclease recognition site are identical to one another and are different from the second nuclease recognition site; and, the first and the third nuclease agent are identical to one another and are different from the second nuclease agent.

19. The method of embodiment 15, wherein the first and the third selection markers are identical.

20. The method of any one of embodiments 1-19, wherein one of the first, the second or the third selection marker imparts resistance to an antibiotic.

21. The method of embodiment 20, wherein the antibiotic comprises G418, hygromycin, blastocidin, neomycin, or puromycin.

22. The method of any one of embodiments 1-19, wherein one of the first, the second or the third selection marker is operably linked to an inducible promoter, and expression of the selection marker is toxic to the cell.

23. The method of embodiment 22, wherein the first, the second or the third selection marker comprises hypoxanthine-guanine phosphoribosyltransferase (HGPRT) or thymidine kinase of Herpes simplex virus (HSV-TK).

24. The method of any one of embodiments 1-23, wherein said cell is a prokaryotic cell.

25. The method of any one of embodiments 1-23, wherein the cell is a eukaryotic cell.

26. The method of embodiment 25, wherein the eukaryotic cell is a mammalian cell.

27. The method of embodiment 26, wherein the mammalian cell is a non-human mammalian cell.

28. The method of embodiment 27, wherein the mammalian cell is from a rodent.

29. The method of embodiment 28, wherein the rodent is a rat or a mouse.

30. The method of any one of embodiments 26-29, wherein the cell is a pluripotent cell.

31. The method of embodiment 26, wherein the mammalian cell is a human induced pluripotent stem (iPS) cell.

32. The method of embodiment 30, wherein the pluripotent cell is a non-human embryonic stem (ES) cell.

33. The method of embodiment 30, wherein the pluripotent cell is a mouse embryonic stem (ES) cell or a rat embryonic stem (ES) cell.

34. The method of any one of embodiments 30-33, wherein the pluripotent cell is a hematopoietic stem cell.

35. The method of any one of embodiments 30-33, wherein the pluripotent cell is a neuronal stem cell.

36. The method of embodiment 26, wherein the mammalian cell is a human fibroblast.

37. The method of embodiment 1 or 2, wherein the combined use of the first targeting vector with the first nuclease agent results in an increased targeting efficiency compared to the use of the first targeting vector alone.

38. The method of embodiment 37, wherein the targeting efficiency of the first targeting vector is increased at least 2-fold compared to the use of the first targeting vector alone.

39. The method of any one of embodiments 1-38, wherein the first or the second nuclease agent comprises an expression construct comprising a nucleic acid sequence encoding the nuclease agent, and wherein the nucleic acid is operably linked to a fourth promoter active in the cell.

40. The method of any one of embodiments 1-39, wherein the first or the second nuclease agent is an mRNA encoding a nuclease.

41. The method of any one of embodiments 1-39, wherein the first or the second nuclease agent is a zinc finger nuclease (ZFN).

42. The method of any one of embodiments 1-39, wherein the first or the second nuclease agent is a Transcription Activator-Like Effector Nuclease (TALEN).

43. The method of any one of embodiments 1-39, wherein the first or the second nuclease agent is a meganuclease.

44. The method of any one of embodiments 1-43, wherein the first or the second nuclease agent comprises a Clustered Regularly Interspaced Short Palindromic Repeats (CRISPR)-associated (Cas) protein and a guide RNA (gRNA).

45. The method of embodiment 44, wherein the guide RNA (gRNA) comprises (a) a Clustered Regularly Interspaced Short Palindromic Repeats (CRISPR) RNA (crRNA) that targets the first, the second, or the third recognition sites; and (b) a trans-activating CRISPR RNA (tracrRNA).

46. The method of embodiment 45, wherein the first or the second recognition sites are immediately flanked by a Protospacer Adjacent Motif (PAM) sequence.

47. The method of embodiment 44, 45 or 46, wherein the genomic locus of interest comprises the nucleotide sequence of SEQ ID NO: 1.

48. The method of embodiment 44, 45, 46 or 47, wherein the Cas protein is Cas9.

49. The method of any one of embodiments 44-46, wherein the gRNA comprises: (a) the chimeric RNA of the nucleic acid sequence of SEQ ID NO: 2; or, (b) the chimeric RNA of the nucleic acid sequence of SEQ ID NO: 3.

50. The method of any one of embodiment 44-46, wherein the crRNA comprises SEQ ID NO: 4; SEQ ID NO: 5; or SEQ ID NO: 6.

51. The method of any one of embodiment 44-46, wherein the tracrRNA comprises SEQ ID NO: 7 or SEQ ID NO: 8.

52. The method of any one of embodiments 1-51, wherein the first, the second, and/or the third recognition site is located in an intron, an exon, a promoter, a promoter regulatory region, or an enhancer region of the first, the second, or the third selection marker.

53. The method of any one of embodiments 1-52, wherein the first target site and the second target site are immediately adjacent to the first recognition site.

54. The method of any one of embodiments 10-19, wherein the first target site and the second target site are about 10 nucleotides to about 14 kb from first recognition site.

55. The method of any one of embodiments 10-19, wherein the third target site and the fourth target site are immediately adjacent to the second recognition site.

56. The method of any one of embodiments 10-19, wherein the third target site and the fourth target site are about 10 nucleotides to about 14 kb from the second recognition site.

57. The method of any one of embodiments 1-56, wherein a sum total of the first homology arm and the second homology arm is at least about 10 kb.

58. The method of any one of embodiments 10-57, wherein a sum total of the third homology arm and the fourth homology arm is at least about 10 kb.

59. The method of any one of embodiments 1-58, wherein the first insert polynucleotide ranges from about 5 kb to about 300 kb in length.

60. The method of any one of embodiments 10-59, wherein the second insert polynucleotide ranges from about 5 kb to about 300 kb in length.

61. The method of any one of embodiments 1-60, wherein integration of the first insert polynucleotide into the target locus results in a knockout, a knock-in, a point mutation, a domain swap, an exon swap, an intron swap, a regulatory sequence swap, a gene swap, or a combination thereof.

62. The method of any one of embodiments 10-61, wherein integration of the second insert polynucleotide into the target locus results in a knockout, a knock-in, a point mutation, a domain swap, an exon swap, an intron swap, a regulatory sequence swap, a gene swap, or a combination thereof.

63. The method of any one of embodiments 1-62, wherein the first insert polynucleotide comprises a polynucleotide of interest comprising a human polynucleotide.

64. The method of any one of embodiments 8-63, wherein the second insert polynucleotide comprises a polynucleotide of interest comprising a human polynucleotide.

65. The method of any one of embodiments 1-64, wherein the first insert polynucleotide comprises a polynucleotide of interest comprising a region of the T cell receptor alpha locus.

66. The method of any one of embodiments 8-65, wherein the second insert polynucleotide comprises a polynucleotide of interest comprising a region of the T cell receptor alpha locus.

67. The method of embodiments 65 or 66, wherein the first or the second insert polynucleotide comprise a polynucleotide of interest comprising at least one variable region gene segment and/or a joining region gene segment of the T cell receptor alpha locus.

68. The method of any one of embodiments 65-67, wherein the region of the T cell receptor alpha locus is from a human.

69. The method of any one of embodiments 1-64, wherein the first insert polynucleotide comprises a polynucleotide of interest comprising an unrearranged human immunoglobulin heavy chain variable region nucleic acid sequence operably linked to a non-human immunoglobulin heavy chain constant region nucleic acid sequence.

70. The method of any one of embodiments 1-69, wherein the identifying step is carried out via a modification of allele (MOA) assay.

71. The method of any one of embodiments 1-65, wherein the first insert polynucleotide comprises a polynucleotide of interest comprising a nucleic acid sequence that is homologous or orthologous to the nucleic acid sequence in a genome of the cell.

72. The method of any one of embodiments 10-71, wherein the second insert polynucleotide comprises a nucleic acid sequence that is homologous or orthologous to the nucleic acid sequence in a genome of the cell.

73. The method of any one of embodiments 1-70, wherein the first insert polynucleotide comprises a polynucleotide of interest comprising an exogenous nucleic acid sequence.

74. The method of any one of embodiments 10-70 or 73, wherein the second insert polynucleotide comprises a polynucleotide of interest comprising an exogenous nucleic acid sequence.

Other non-limiting embodiments include:

1. A method for modifying a target locus of interest in a cell, comprising: (a) providing the cell comprising a first target locus comprising a nucleic acid encoding a first selection marker operably linked to a first promoter, (b) introducing into the cell: (i) one or more expression constructs encoding a Cas protein and a first guide RNA (gRNA), each of which is operably linked to a promoter active in the cell, wherein the Cas protein induces a nick or a double-strand break at a first gRNA target site in the first nucleic acid, thereby disrupting expression or activity of the first selection marker; and (ii) a first targeting vector comprising a first insert nucleic acid comprising a second nucleic acid that encodes a second selection marker operably linked to a second promoter, wherein the first insert nucleic acid is flanked by a first and a second homology arm corresponding to a first and a second target site located in the first target locus; and (c) identifying a modified cell comprising the first insert nucleic acid at the first target locus, wherein the modified cell has the activity of the second selection marker but does not have the activity of the first selection marker, and wherein the first and the second selection markers are different.

2. The method of embodiment 1, wherein the first gRNA does not hybridize to the first insert nucleic acid.

3. The method of embodiment 1, wherein the target locus of interest is located in the genome of the cell.

4. The method of embodiment 1, wherein the target locus of interest is located in a vector in the cell.

5. The method of embodiment 1, wherein identifying step (c) comprises culturing the cell under conditions that allow identification of the modified cell that has activity of the second selection marker but does not have the activity of the first selection marker.

6. The method of embodiment 1, further comprising: (d) introducing into the modified cell comprising the first insert nucleic acid at the first target locus: (i) one or more nucleic acids encoding the Cas protein and a second gRNA, each of which operably linked to the promoter active in the modified cell, wherein the Cas protein induces the nick or double-strand break at a second gRNA target site in the first insert nucleic acid comprising the second nucleic acid, thereby disrupting expression or activity of the second selection marker; and (ii) a second targeting vector comprising a second insert nucleic acid comprising a third nucleic acid encoding a third selection marker operably linked to a third promoter, wherein the second insert nucleic acid is flanked by third and fourth homology arms corresponding to a third and a fourth target site located in a second target locus; and (e) identifying a second modified cell comprising the second insert nucleic acid at the second target locus, wherein the second modified cell has the activity of the third selection marker but does not have the activity of the second selection marker, wherein the second and the third selection markers are different.

7. The method of embodiment 6, wherein the first and the second target loci are located immediately adjacent to each other.

8. The method of embodiment 6, wherein the first or the second target locus is located about 10 nucleotides to about 14 kb from the first or the second gRNA target site.

9. The method of embodiment 8, wherein the second gRNA does not hybridize to the second insert nucleic acid.

10. The method of embodiment 6, wherein identifying step (e) comprises culturing the modified cell under conditions that allow identification of the second modified cell that has activity of the third selection marker but does not have the activity of the second selection marker.

11. The method of embodiment 6, further comprising: (f) introducing into the second modified cell comprising the second insert nucleic acid at the second target locus: (i) the one or more expression constructs encoding the Cas protein and a third gRNA, each of which operably linked to the promoter active in the second modified cell, wherein the Cas protein induces the nick or double-strand break at a third gRNA target site in the second insert nucleic acid comprising the third nucleic acid, thereby disrupting expression or activity of the third selection marker; and (ii) a third targeting vector comprising a third insert nucleic acid comprising a fourth nucleic acid that encodes a fourth selection marker operably linked to a fourth promoter, wherein the third insert nucleic acid is flanked by fifth and six homology arms corresponding to fifth and sixth target sites located in a third target locus; and (g) identifying a third modified cell comprising the third insert nucleic acid at the third target locus, wherein the third modified cell has the activity of the fourth selection marker but does not have the activity of the third selection marker, wherein the third and the fourth selection markers are different.

12. The method of embodiment 11, wherein the second and third target loci are located immediately adjacent to each other.

13. The method of embodiment 11, wherein the second or the third target locus is located about 10 nucleotides to about 14 kb from the first or the second gRNA target site.

14. The method of any one of embodiments 1-13, wherein the first, the second, the third, or the fourth marker imparts resistance to an antibiotic.

15. The method of embodiment 14, wherein the antibiotic comprises G418, hygromycin, blastocidin, neomycin, or puromycin.

16. The method of any one of embodiments 1-13, wherein the first, the second, the third, or the fourth selection markers comprise hypoxanthine-guanine phosphoribosyltransferase (HGPRT) or thymidine kinase of Herpes simplex virus (HSV-TK).

17. The method of embodiment 1, 6, or 11, wherein the first, the second, or the third gRNAs comprises (i) a nucleotide sequence that hybridizes to the first, the second or the third gRNA target site and (ii) a trans-activating CRISPR RNA (tracrRNA).

18. The method of embodiment 1, 6, or 11, wherein the first, the second, or the third target locus is located in close proximity to the first, the second or the third gRNA target site such that the nick or the double-strand break at the gRNA target site promotes homologous recombination of the targeting vector at the target locus.

19. The method of embodiment 1, 6, or 11, wherein the Cas protein is Cas9.

20. The method of embodiment 19, wherein the first, the second, or the third gRNA target site is immediately flanked by a Protospacer Adjacent Motif (PAM) sequence.

21. The method of embodiment 1, 6, or 11, wherein said cell is a prokaryotic cell.

22. The method of embodiments 1, 6, and 11, wherein the cell is a eukaryotic cell.

23. The method of embodiment 22, wherein the eukaryotic cell is a mammalian cell.

24. The method of embodiment 23, wherein the mammalian cell is a fibroblast cell.

25. The method of embodiment 23, wherein the mammalian cell is a non-human mammalian cell.

26. The method of embodiment 23, wherein the mammalian cell is from a rodent.

27. The method of embodiment 26, wherein the rodent is a rat, a mouse, or a hamster.

28. The method of embodiment 22, wherein the eukaryotic cell is a pluripotent cell.

29. The method of embodiment 28, wherein the pluripotent cell is a hematopoietic stem cell or a neuronal stem cell.

30. The method of embodiment 28, wherein pluripotent cell is a human induced pluripotent stem (iPS) cell.

31. The method of embodiment 28, wherein the pluripotent cell is a mouse embryonic stem (ES) cell or a rat embryonic stem (ES) cell.

32. The method of any one of embodiments 1, 6, and 11, wherein the first, the second, or the third gRNA target site is located in an intron, an exon, a promoter, or a promoter regulatory region in the first, the second, or the third nucleic acid that encodes the first, the second, or the third selection marker.

33. The method of embodiment 1, 6, or 11, wherein the first, second, or third targeting vector is at least about 10 kb.

34. The method of embodiment 1, 6, or 11, wherein the first, the second, or the third insert nucleic acid ranges from about 5 kb to about 300 kb.

35. The method of embodiment 1, 6, or 11, wherein the first, second, or third insert nucleic acid comprises a genomic region of the human T cell receptor alpha locus.

36. The method of claim 35, wherein the genomic region comprises at least one variable region gene segment and/or a joining region gene segment of the human T cell receptor alpha locus.

37. The method of embodiment 6, wherein the first and the third selection markers are the same.

38. The method of embodiment 11, wherein the first and the third selection markers are the same and the second and the fourth selection markers are the same.

39. The method of embodiment 38, wherein the first and the third gRNAs are the same.

40. The method of embodiment 1, 6, 37, 38, or 39, wherein the gRNA is specific for a hygromycin or neomycin resistance gene.

41. The method of embodiment 40 wherein the gRNA specific for a neomycin resistance gene is encoded by a nucleic acid comprising the nucleotide sequence set forth in SEQ ID NO: 13, 14, 15, or 16.

42. The method of embodiment 40 wherein the gRNA specific for a hygromycin resistance gene is encoded by a nucleic acid comprising the nucleotide sequence set forth in SEQ ID NO: 17, 18, 19, or 20.

43. The method of embodiment 6, 37, 38, or 39, wherein a) the first gRNA is encoded by a nucleic acid comprising the nucleotide sequence set forth in SEQ ID NO: 13, 14, 15, or 16 and the second gRNA is encoded by a nucleic acid comprising the nucleotide sequence set forth in SEQ ID NO: 17, 18, 19, or 20; or b) the first gRNA is encoded by a nucleic acid comprising the nucleotide sequence set forth in SEQ ID NO: 17, 18, 19, or 20 and the second gRNA is encoded by a nucleic acid comprising the nucleotide sequence set forth in SEQ ID NO: 13, 14, 15, or 16.

The following examples are offered by way of illustration and not by way of limitation.

EXAMPLES

Figure 2:
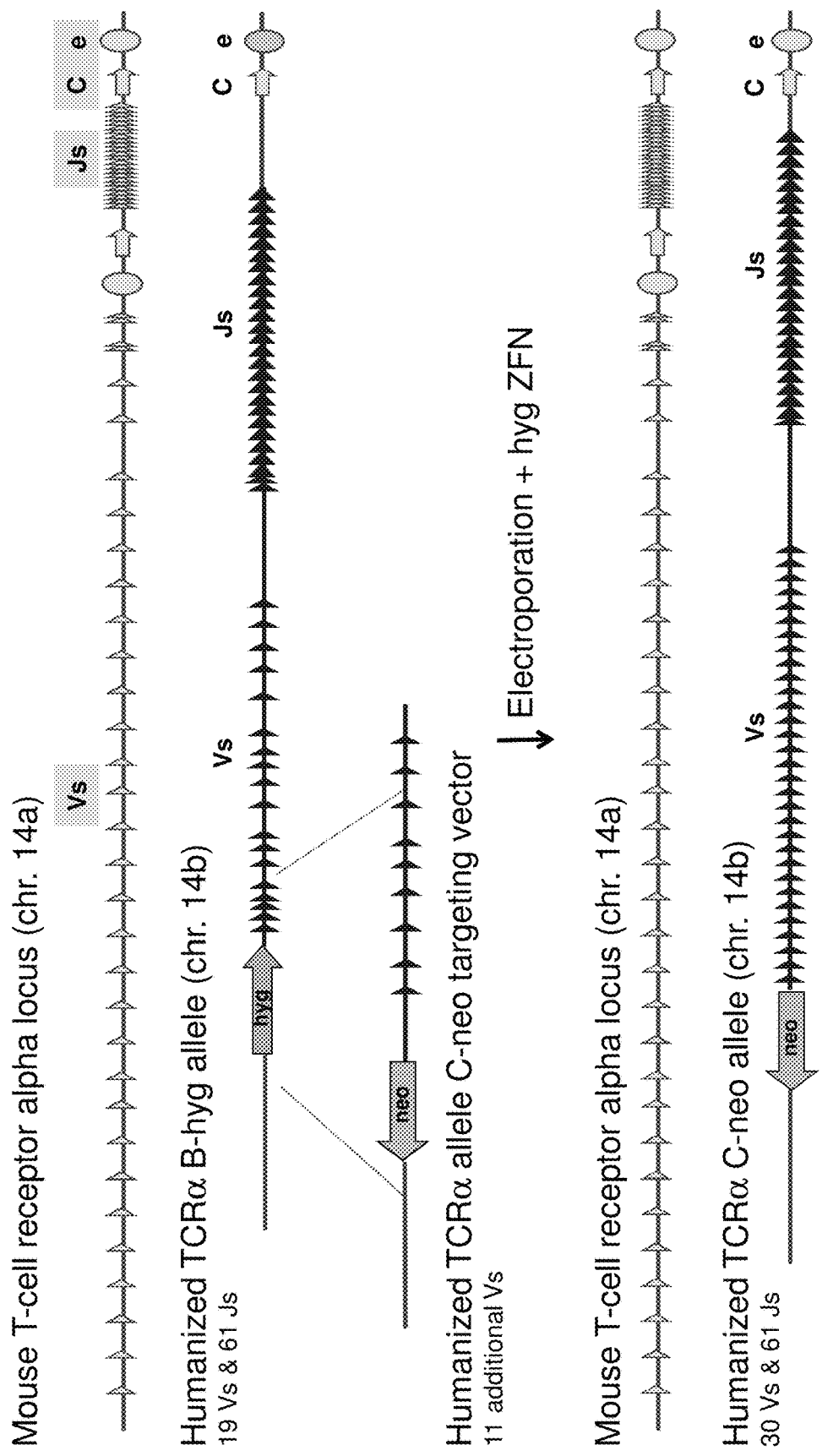
FIG. 2 provides a schematic for a genomic targeting event in which a cell having a heterozygous modification of the TCR alpha locus on mouse chromosome 14, one allele of which is the humanized TCR alpha B-hyg allele, comprising a hygromycin selection cassette located upstream of 19 human V gene segments and 61 human J gene segments is targeted with a humanized TCR alpha allele C-neo targeting vector, comprising a neomycin selection cassette and a fragment of greater than 100 kb comprising 11 additional human variable gene segments. Electroporation of the allele C-neo targeting vector and plasmids expressing the two halves of a zinc finger nuclease (ZFN) pair that targets the hygromycin cassette in the TCR alpha B-hyg allele generated a modified TCR alpha locus (allele C-neo) comprising, from 5' to 3', a neomycin cassette, 30 human V gene segments, and 61 human J gene segments located upstream of the endogenous constant region nucleotide sequence. The targeting event precisely inserted more than 100 kb of human TCR alpha gene sequence into the mouse TCR alpha locus.

The sequential gene targeting experiments depicted in FIGS. 1 and 2 demonstrated the value of combining a large BAC-based targeting vector (LTVEC) with a zinc finger nuclease (ZFN) designed to recognize and cleave a target sequence in a drug selection cassette.

For the first step in the sequential targeting (FIG. 1), an LTVEC was constructed to create a modification (TCRα B-hyg allele) that inserts 136 kb of DNA encoding 11 variable (V) domains of the human T-cell receptor alpha (TCRα) into the corresponding mouse TCRα locus. 0.02 mg of the constructed LTVEC was electroporated into 10 million mouse embryonic stem (ES) cells that carried a previously created modification (TCRα A-neo allele) at the TCRα locus, which replaced the mouse variable (V) and joining (J) gene segments with human Vs and Js. After recovery of the electroporated ES cell in a growth medium, hygromycin was added to select for colonies that were derived from cells that had incorporated the LTVEC into their genomes. Modification of allele (MOA) screening of isolated colonies resulted in the identification of four correctly targeted clones among 136 hygromycin resistant colonies screened, for a targeting efficiency of 2.9% (Table 1, Experiment 1). In addition to insertion of the 11 additional Vs, the correctly targeted clones had a hygromycin resistance cassette (hyg$^r$) that had replaced the neomycin (G418) resistance cassette (neo$^r$).

Experiment 2 was identical to Experiment 1 except for the additions of 0.02 mg each of two plasmids that expressed each half of the Neo-ZFN(1,2), which binds to recognition sequences in the neor gene and catalyzes a double-strand break in the DNA. The inclusion of the Neo-ZFN(1,2) resulted in 55 correctly targeted clones out of 568 hygromycin resistant clones screened, for a targeting efficiency of 9.7%, which represents a 3.3-times higher targeting efficiency compared with an electroporation with the LTVEC alone (Table 1, compare Experiments 1 and 2).

Experiment 3 was identical to Experiment 2 except that plasmids encoding Neo-ZFN(3,4) replaced those for Neo-ZFN(1,2). The inclusion of the Neo-ZFN(3,4) resulted in 42 correctly targeted clones out of 360 hygromycin resistant clones screened, for a targeting efficiency of 11.7%, which represents a 4-times higher in targeting efficiency compared with an electroporation with the LTVEC alone (Table 1, compare Experiments. 1 and 3).

For the second step in the sequential targeting (FIG. 2), electroporation of 0.002 mg of an LTVEC designed to create a modification (TCRα C-neo allele) that inserts 157 kb of DNA encoding 11 additional human TCRα variable (V) domains different from those in the TCRα A-neo or B-hyg alleles into 10 million mouse embryonic stem (ES) cells that carried the TCRα B-hyg allele made in the first step of the sequential targeting (FIG. 1), introduced the LTVEC into the ES cells. After recovery of the electroporated ES cell in a growth medium, G418 was added to select for colonies that were derived from cells that had incorporated the LTVEC into their genomes. MOA screening of isolated colonies resulted in the identification of two correctly targeted clones among 192 G418 resistant colonies screened, for a targeting efficiency of 1.0% (Table 1, Experiment 4). In addition to insertion of the 11 additional Vs, the correctly targeted clones had a neor cassette that had replaced the hygr cassette.

Experiment 5 was identical to Experiment 4 except for the additions of 0.02 mg each of two plasmids that expressed each half of the Hyg-ZFN(1,2), which binds to recognition sequences in hygr and catalyzes a double-strand break in the DNA. The inclusion of the Hyg-ZFN(1,2) resulted in 40 correctly targeted clones out of 192 G418 resistant clones screened, for a targeting efficiency of 21%, which represents a 21-times higher targeting efficiency compared with an electroporation with the LTVEC alone (Table 1, compare Experiments. 4 and 5).

Experiment 6 was identical to Experiment 5 except that plasmids encoding Hyg-ZFN(3,4) replaced those for Hyg-ZFN(1,2). The inclusion of the Hyg-ZFN(3,4) resulted in 42 correctly targeted clones out of 192 hygromycin resistant clones screened, for a targeting efficiency of 22%, which represents a 22-times higher targeting efficiency compared with an electroporation with the LTVEC alone (Table 1, compare Experiments. 4 and 6).

The experiments summarized in Table 1 established that the inclusion of ZFNs that target the neo$^r$ or hyg$^r$ selection cassettes with LTVECs in sequential targeting experiments can enhance the targeting efficiency by a factor of 3 to 20 times compared with targeting experiments that include only the LTVEC. The enhanced targeting efficiencies produced by the inclusion of the ZFNs in the sequential targeting experiments promoted the correct intended insertion of very large pieces (136 kb and 157 kb) of human DNA precisely at the desired chromosomal position of a previously modified allele. The ZFN-enhanced targeting greatly increases the probability of success in a targeting project and delivers a significant savings in time, labor, and material costs for ES cell screening.

TABLE 1

Enhancement of sequential gene targeting by Zinc Finger Nucleases that recognize neo$^r$ and hyg$^r$ sequences

| Expt. | Electroporated DNA | Recipient ES cell | Targeting efficiency[1] (%) | Enhancement of targeting[2] |
|---|---|---|---|---|
| 1 | i. Humanized TCRα allele B-hyg LTVEC[3] | Humanized TCRα A-neo allele[3] | 2.9 (4/136) | n.a. |
| 2 | i. Humanized TCRα allele B-hyg LTVEC ii. Neo ZFN1 plasmid[4] iii. Neo-ZFN2 plasmid[4] | Humanized TCRα A neo allele | 9.7 (55/568) | 3.3X |
| 3 | i. Humanized TCRa allele B-hyg LTVEC ii. Neo-ZFN3 plasmid[5] iii. Neo-ZFN4 plasmid[5] | Humanized TCRα A-neo allele | 11.7 (42/360) | 4.0X |
| 4 | i. Humanized TCRα allele C-neo LTVEC[6] | Humanized TCRα B-hyg allele[6] | 1.0 (2/192) | n.a. |
| 5 | i. Humanized TCRα allele C-neo LTVEC ii. Hyg-ZFN1 plasmid[7] iii. Hyg -ZFN2 plasmid[7] | Humanized TCRα B-hyg allele | 21 (40/192) | 21X |
| 6 | i. Humanized TCRα allele B-hyg LTVEC ii. Hyg-ZFN3 plasmid[8] iii. Hyg-ZFN4 plasmid[8] | Humanized TCRα B-hyg allele | 22 (42/192) | 22X |

[1]Ratio of correctly targeted clones to total clones screened (shown in parentheses) expressed as a percentage
[2]Ratio of the targeting efficiency of an experiment that combined a targeting vector with ZFN plasmids to an experiment that used the targeting vector alone
[3]See FIG. 1Neo-ZFN(1, 2)(see FIG. 3) NUCLEASE BINDING SITE/cutsite: GGGCGCCCGGTTCTTTTT/gtcaag/ACCGACCTGTCCGGTG (SEQ ID NO: 9)
[5]Neo-ZFN(3, 4)(see FIG. 3) NUCLEASE BINDING SITE/cutsite: CCGGTTCTTTTTGTC/aagacc/GACCTGTCCGGTGCC (SEQ ID NO: 10)
[6]See FIG. 2Hyg-ZFN(1, 2)(see FIG. 3) NUCLEASE BINDING SITE/cutsite: TGCGATCGCTGCGGCCGA/tcttag/CCAGACGAGCGGGTTCGG (SEQ ID NO: 11)
[8]Hyg-ZFN(3, 4)(see FIG. 3) NUCLEASE BINDING SITE/cutsite: CGCTGCGGCCGATCT/tagcca/GACGAGCGGGTTCGG (SEQ ID NO: 12)

TABLE 2

Sample gRNAs for use in targeting Neomycin and Hygromycin resistance markers

| SEQ ID NO | | gRNA |
|---|---|---|
| 13 | Neo Crispr#1 | UGCGCAAGGAACGCCCGUCG |
| 14 | Neo Crispr#2 | GGCAGCGCGGCUAUCGUGGC |
| 15 | Neo Crispr#3 | ACGAGGCAGCGCGGCUAUCG |
| 16 | Neo Crispr#4 | GCUCUGAUGCCGCCGUGUUC |
| 17 | Hyg Crispr#1 | ACGAGCGGGUUCGGCCCAUU |
| 18 | Hyg Crispr#6 | CUUAGCCAGACGAGCGGGUU |
| 19 | Hyg Crispr#10 | GCCGAUCUUAGCCAGACGAG |
| 20 | Hyg Crispr#16 | CGACCUGAUGCAGCUCUCGG |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Unless otherwise apparent from the context of any embodiment, aspect, step or feature of the invention can be used in combination with any other. Reference to a range includes any integers within the range, any subrange within the range. Reference to multiple ranges includes composites of such ranges.

That which is claimed:

1. A method for serial modification of a target locus in a cell, comprising:
   (a) providing the cell comprising the target locus, wherein the target locus comprises a first selection cassette comprising: (1) a nucleic acid encoding a first selection marker; and (2) a first nuclease recognition site for a first nuclease agent, wherein the first nuclease recognition site is located in a coding region of the first selection marker or any non-protein-coding region of the first selection marker;
   (b) introducing into the cell:
      (i) the first nuclease agent, wherein the first nuclease agent induces a nick or a double-strand break at the first nuclease recognition site; and
      (ii) a first targeting vector comprising a first insert polynucleotide flanked by a first homology arm corresponding to a first target site located in the target locus and a second homology arm corresponding to a second target site located in the target locus, wherein the first insert polynucleotide comprises a second selection cassette comprising: (1) a nucleic acid encoding a second selection marker, wherein the first selection marker and the second selection marker are different; and (2) a second nuclease recognition site for a second nuclease agent, wherein the second nuclease recognition site is located in a coding region of the second selection marker or any non-protein-coding region of the second selection marker; and
   (c) identifying a modified cell comprising the first insert polynucleotide at the target locus, wherein the modified cell has the activity of the second selection marker but does not have the activity of the first selection marker;
   (d) introducing into the modified cell:
      (i) the second nuclease agent, wherein the second nuclease agent induces a nick or a double-strand break at the second nuclease recognition site; and
      (ii) a second targeting vector comprising a second insert polynucleotide flanked by a third homology arm corresponding to a third target site located in the target locus and a fourth homology arm corresponding to a fourth target site located in the target locus, wherein the second insert polynucleotide comprises a third selection cassette comprising: (1) a nucleic acid encoding a third selection marker, wherein the first selection marker and the third selection marker are identical; and (2) a third nuclease recognition site for a third nuclease agent, wherein the third nuclease recognition site is identical to the first nuclease recognition site and different from the second nuclease recognition site, and the first nuclease agent and the third nuclease agent are identical to one another and are different from the second nuclease agent; and
   (e) identifying at least one cell comprising the second insert polynucleotide integrated at the target locus, wherein the at least one cell has the activity of the third selection marker but does not have the activity of the second selection marker.

2. The method of claim 1, wherein:
(I) the identifying step (c) comprises:
   (i) culturing the cell under conditions that allow identification of cells that do not have the activity of the first selection marker; or
   (ii) identifying at least one cell comprising the first insert polynucleotide integrated at the first and second target sites; and/or
(II) the identifying step (e) comprises:
   (i) culturing the cell under conditions that allow identification of cells that do not have the activity of the second selection marker; or
   (ii) identifying at least one cell comprising the second insert polynucleotide integrated at the third and fourth target sites.

3. The method of claim 1, wherein the identifying step (c) is carried out via a modification of allele (MOA) assay, and/or the identifying step (e) is carried out via a MOA assay.

4. The method of claim 1, wherein the first selection cassette in step (a) is flanked by the first target site and the second target site, and/or wherein the second selection cassette in the modified cell in step (c) is flanked by the third target site and the fourth target site.

5. The method of claim 1, wherein the first selection marker or the second selection marker imparts resistance to an antibiotic.

6. The method of claim 1, wherein the first selection marker or the second selection marker is operably linked to an inducible promoter, and expression of the inducible selection marker is toxic to the cell.

7. The method of claim 1, wherein the combined use of the first targeting vector with the first nuclease agent increases targeting efficiency at least two-fold compared to the use of the first targeting vector alone.

8. The method of claim 1, wherein the first nuclease agent or the second nuclease agent comprises an expression construct comprising a nucleic acid sequence encoding the nuclease agent, wherein the nucleic acid sequence encoding the nuclease agent is operably linked to a promoter active in the cell.

9. The method of claim 1, wherein the first nuclease agent or the second nuclease agent is a zinc finger nuclease (ZFN), a Transcription Activator-Like Effector Nuclease (TALEN), a meganuclease, or a Clustered Regularly Interspaced Short Palindromic Repeats (CRISPR)-associated (Cas) protein and a guide RNA (gRNA).

10. The method of claim 9, wherein the first nuclease agent or the second nuclease agent is the ZFN, and the first nuclease recognition site or the second nuclease recognition site comprises any one of SEQ ID NOS: 9-12.

11. The method of claim 9, wherein the first nuclease agent or the second nuclease agent is the Cas protein and the gRNA, wherein the Cas protein is Cas9, wherein the gRNA comprises a Clustered Regularly Interspaced Short Palindromic Repeats (CRISPR) RNA (crRNA) that targets the first nuclease recognition site or the second nuclease recognition site and a trans-activating CRISPR RNA (tracrRNA), and wherein the first nuclease recognition site or the second nuclease recognition site is immediately flanked by a Protospacer Adjacent Motif (PAM) sequence.

12. The method of claim 11, wherein the gRNA comprises any one of SEQ ID NOS: 13-20.

13. The method of claim 11, wherein the gRNA comprises SEQ ID NO: 2, 3, 4, 5, 6, 7, or 8.

14. The method of claim 1, wherein the first nuclease recognition site is located in an intron, an exon, a promoter, a promoter regulatory region, or an enhancer region of the first selection marker, and the second nuclease recognition site is located in an intron, an exon, a promoter, a promoter regulatory region, or an enhancer region of the second selection marker.

15. The method of claim 1, wherein the first selection marker imparts resistance to neomycin, the first nuclease agent is a zinc finger nuclease, and the first nuclease recognition site comprises SEQ ID NO: 9 or 10, and wherein the second selection marker imparts resistance to hygromycin, the second nuclease agent is a zinc finger nuclease, and the second nuclease recognition site comprises SEQ ID NO: 11 or 12.

16. The method of claim 1, wherein the first selection marker imparts resistance to neomycin, and the first nuclease agent is a Cas9 protein and a guide RNA comprising any one of SEQ ID NOS: 13-16, and wherein the second selection marker imparts resistance to hygromycin, and the second nuclease agent is a Cas9 protein and a guide RNA comprising any one of SEQ ID NOS: 17-20.

17. The method of claim 16, wherein the first selection marker imparts resistance to neomycin, and the first nuclease agent is the Cas9 protein and the guide RNA comprising SEQ ID NO: 13, and wherein the second selection marker imparts resistance to hygromycin, and the second nuclease agent is the Cas9 protein and the guide RNA comprising SEQ ID NO: 17.

18. The method of claim 1, wherein:
(I) the first target site and the second target site are immediately adjacent to the first nuclease recognition site; and/or
(II) the third target site and the fourth target site are immediately adjacent to the second nuclease recognition site.

19. The method of claim 1, wherein:
(I) the first target site and the second target site are about 10 nucleotides to about 14 kb from the first nuclease recognition site; and/or
(II) the third target site and the fourth target site are about 10 nucleotides to about 14 kb from the second nuclease recognition site.

20. The method of claim 1, wherein:
(I) the sum total of the first homology arm and the second homology arm is at least about 10 kb; and/or
(II) the sum total of the third homology arm and the fourth homology arm is at least about 10 kb.

21. The method of claim 1, wherein:
(I) the first insert polynucleotide ranges from about 5 kb to about 300 kb in length; and/or
(II) the second insert polynucleotide ranges from about 5 kb to about 300 kb in length.

22. The method of claim 1, wherein the first insert polynucleotide further comprises a first polynucleotide of interest, and/or the second insert polynucleotide further comprises a second polynucleotide of interest.

23. The method of claim 22, wherein:
(I) the first polynucleotide of interest comprises a human polynucleotide; and/or
(II) the second polynucleotide of interest comprises a human polynucleotide.

24. The method of claim 23, wherein the first polynucleotide of interest and/or the second polynucleotide of interest comprises a polynucleotide encoding a region of a T cell receptor.

25. The method of claim 24, wherein the T cell receptor is a T cell receptor alpha.

26. The method of claim 23, wherein the first polynucleotide of interest and/or the second polynucleotide of interest comprises a genomic nucleic acid sequence that encodes a human immunoglobulin heavy chain variable region amino acid sequence.

27. The method of claim 23, wherein the first polynucleotide of interest and/or the second polynucleotide of interest comprises a genomic nucleic acid sequence that encodes a human immunoglobulin light chain variable region amino acid sequence.

28. The method of claim 27, wherein the genomic nucleic acid sequence comprises an unrearranged human λ and/or κ light chain variable region nucleic acid sequence.

29. The method of claim 27, wherein the genomic nucleic acid sequence comprises a rearranged human λ and/or κ light chain variable region nucleic acid sequence.

30. The method of claim 23, wherein the first polynucleotide of interest and/or the second polynucleotide of interest comprises at least one disease allele.

31. The method of claim 1, wherein:
(I) the first insert polynucleotide comprises:
  (i) a first polynucleotide of interest comprising a nucleic acid sequence that is homologous or orthologous to a nucleic acid sequence in the genome of the cell; or
  (ii) a first polynucleotide of interest comprising an exogenous nucleic acid sequence; and/or
(II) the second insert polynucleotide comprises:
  (i) a second polynucleotide of interest that is homologous or orthologous to a nucleic acid sequence in the genome of the cell; or
  (ii) a second polynucleotide of interest comprising an exogenous nucleic acid sequence.

32. The method of claim 1, wherein:
(I) integration of the first insert polynucleotide into the target locus results in a knockout, a knock-in, a point mutation, a domain swap, an exon swap, an intron swap, a regulatory sequence swap, a gene swap, or a combination thereof; and/or
(II) integration of the second insert polynucleotide into the target locus results in a knockout, a knock-in, a point mutation, a domain swap, an exon swap, an intron swap, a regulatory sequence swap, a gene swap, or a combination thereof.

33. The method of claim 1, wherein the target locus is in the genome of the cell or is located in a vector in the cell.

34. The method of claim 33, wherein the target locus comprises an immunoglobulin locus.

35. The method of claim 33, wherein the target genomic locus comprises a T cell receptor locus.

36. The method of claim 35, wherein the T cell receptor locus is a T cell receptor alpha locus.

37. The method of claim 1, wherein the cell is a mouse embryonic stem (ES) cell.

38. The method of claim 1, wherein the cell is a rat embryonic stem (ES) cell.

39. The method of claim 37, further comprising:
(f) introducing the cell produced in step (e) into a mouse host embryo at a pre-morula stage to produce a modified host embryo; and
(g) implanting the modified host embryo into a surrogate mother to generate an F0 generation mouse derived from the cell produced in step (e).

40. The method of claim 38, further comprising:
(f) introducing the cell produced in step (e) into a rat host embryo at a pre-morula stage to produce a modified host embryo; and
(g) implanting the modified host embryo into a surrogate mother to generate an F0 generation rat derived from the cell produced in step (e).

41. The method of claim 13, wherein the gRNA comprises SEQ ID NO: 3 or SEQ ID NO: 7.

42. The method of claim 1, wherein:
(I) the nick or the double-strand break induced by the first nuclease agent disrupts the activity of the first selection marker, or wherein insertion of the first insert polynucleotide at the target locus disrupts the activity of the first selection marker; and/or
(II) the nick or the double-strand break induced by the second nuclease agent disrupts the activity of the second selection marker, or wherein insertion of the second insert polynucleotide at the target locus disrupts the activity of the second selection marker.

43. The method of claim 5, wherein the first and third selection markers impart resistance to neomycin and the second selection marker imparts resistance to hygromycin, or
wherein the first and third selection markers impart resistance to hygromycin and the second selection marker imparts resistance to neomycin.

\* \* \* \* \*